United States Patent
Joshi

(10) Patent No.: US 12,394,086 B2
(45) Date of Patent: Aug. 19, 2025

(54) ACCURACY CHECK AND AUTOMATIC CALIBRATION OF TRACKED INSTRUMENTS

(71) Applicant: GLOBUS MEDICAL, INC., Audubon, PA (US)

(72) Inventor: Sanjay M. Joshi, Andover, MA (US)

(73) Assignee: Globus Medical, Inc., Audubon, PA (US)

( * ) Notice: Subject to any disclaimer, the term of this patent is extended or adjusted under 35 U.S.C. 154(b) by 514 days.

(21) Appl. No.: 17/662,666

(22) Filed: May 10, 2022

(65) Prior Publication Data

US 2023/0363827 A1 Nov. 16, 2023

(51) Int. Cl.
*G06T 7/73* (2017.01)
*A61B 34/20* (2016.01)
*A61B 90/00* (2016.01)

(52) U.S. Cl.
CPC .............. *G06T 7/74* (2017.01); *A61B 34/20* (2016.02); *A61B 2034/2055* (2016.02); *A61B 2034/2061* (2016.02); *A61B 2034/2065* (2016.02); *A61B 2034/2072* (2016.02); *A61B 2090/3764* (2016.02)

(58) Field of Classification Search
None
See application file for complete search history.

(56) References Cited

U.S. PATENT DOCUMENTS

| | | | |
|---|---|---|---|
| 4,150,293 A | 4/1979 | Franke | |
| 5,246,010 A | 9/1993 | Gazzara et al. | |
| 5,354,314 A | 10/1994 | Hardy et al. | |
| 5,397,323 A | 3/1995 | Taylor et al. | |
| 5,598,453 A | 1/1997 | Baba et al. | |
| 5,772,594 A | 6/1998 | Barrick | |
| 5,791,908 A | 8/1998 | Gillio | |
| 5,820,559 A | 10/1998 | Ng et al. | |
| 5,825,982 A | 10/1998 | Wright et al. | |
| 5,887,121 A | 3/1999 | Funda et al. | |
| 5,911,449 A | 6/1999 | Daniele et al. | |
| 5,951,475 A | 9/1999 | Gueziec et al. | |

(Continued)

OTHER PUBLICATIONS

US 8,231,638 B2, 07/2012, Swarup et al. (withdrawn)

*Primary Examiner* — Jason M Ip
*Assistant Examiner* — Renee C Langhals

(57) ABSTRACT

A system configured to perform an accuracy check of a tracked instrument can include a processing circuitry and memory coupled to the processing circuitry. The memory can include instructions to cause the system to perform operations. The operations can include determining a virtual position of a display device. The operations can further include determining a virtual position of the tracked instrument. The operations can further include determining a point of contact on the display device between the tracked instrument and the display device. The operations can further include determining an expected point of contact on the display device between the tracked instrument and the display device based on the virtual position of the display device and the virtual position of the tracked instrument. The operations can further include determining whether the tracked instrument is accurate based on a difference between the point of contact and the expected point of contact.

8 Claims, 15 Drawing Sheets

(56) References Cited

U.S. PATENT DOCUMENTS

| | | |
|---|---|---|
| 5,987,960 A | 11/1999 | Messner et al. |
| 6,012,216 A | 1/2000 | Esteves et al. |
| 6,031,888 A | 2/2000 | Ivan et al. |
| 6,033,415 A | 3/2000 | Mittelstadt et al. |
| 6,080,181 A | 6/2000 | Jensen et al. |
| 6,106,511 A | 8/2000 | Jensen |
| 6,122,541 A | 9/2000 | Cosman et al. |
| 6,144,875 A | 11/2000 | Schweikard et al. |
| 6,157,853 A | 12/2000 | Blume et al. |
| 6,167,145 A | 12/2000 | Foley et al. |
| 6,167,292 A | 12/2000 | Badano et al. |
| 6,201,984 B1 | 3/2001 | Funda et al. |
| 6,203,196 B1 | 3/2001 | Meyer et al. |
| 6,205,411 B1 | 3/2001 | DiGioia, III et al. |
| 6,212,419 B1 | 4/2001 | Blume et al. |
| 6,231,565 B1 | 5/2001 | Tovey et al. |
| 6,236,875 B1 | 5/2001 | Bucholz et al. |
| 6,246,900 B1 | 6/2001 | Cosman et al. |
| 6,301,495 B1 | 10/2001 | Gueziec et al. |
| 6,306,126 B1 | 10/2001 | Montezuma |
| 6,312,435 B1 | 11/2001 | Wallace et al. |
| 6,314,311 B1 | 11/2001 | Williams et al. |
| 6,320,929 B1 | 11/2001 | Von Der Haar |
| 6,322,567 B1 | 11/2001 | Mittelstadt et al. |
| 6,325,808 B1 | 12/2001 | Bernard et al. |
| 6,340,363 B1 | 1/2002 | Bolger et al. |
| 6,377,011 B1 | 4/2002 | Ben-Ur |
| 6,379,302 B1 | 4/2002 | Kessman et al. |
| 6,402,762 B2 | 6/2002 | Hunter et al. |
| 6,424,885 B1 | 7/2002 | Niemeyer et al. |
| 6,447,503 B1 | 9/2002 | Wynne et al. |
| 6,451,027 B1 | 9/2002 | Cooper et al. |
| 6,477,400 B1 | 11/2002 | Barrick |
| 6,484,049 B1 | 11/2002 | Seeley et al. |
| 6,487,267 B1 | 11/2002 | Wolter |
| 6,490,467 B1 | 12/2002 | Bucholz et al. |
| 6,490,475 B1 | 12/2002 | Seeley et al. |
| 6,499,488 B1 | 12/2002 | Hunter et al. |
| 6,501,981 B1 | 12/2002 | Schweikard et al. |
| 6,507,751 B2 | 1/2003 | Blume et al. |
| 6,535,756 B1 | 3/2003 | Simon et al. |
| 6,560,354 B1 | 5/2003 | Maurer, Jr. et al. |
| 6,565,554 B1 | 5/2003 | Niemeyer |
| 6,587,750 B2 | 7/2003 | Gerbi et al. |
| 6,614,453 B1 | 9/2003 | Suri et al. |
| 6,614,871 B1 | 9/2003 | Kobiki et al. |
| 6,619,840 B2 | 9/2003 | Rasche et al. |
| 6,636,757 B1 | 10/2003 | Jascob et al. |
| 6,645,196 B1 | 11/2003 | Nixon et al. |
| 6,666,579 B2 | 12/2003 | Jensen |
| 6,669,635 B2 | 12/2003 | Kessman et al. |
| 6,701,173 B2 | 3/2004 | Nowinski et al. |
| 6,757,068 B2 | 6/2004 | Foxlin |
| 6,782,287 B2 | 8/2004 | Grzeszczuk et al. |
| 6,783,524 B2 | 8/2004 | Anderson et al. |
| 6,786,896 B1 | 9/2004 | Madhani et al. |
| 6,788,018 B1 | 9/2004 | Blumenkranz |
| 6,804,581 B2 | 10/2004 | Wang et al. |
| 6,823,207 B1 | 11/2004 | Jensen et al. |
| 6,827,351 B2 | 12/2004 | Graziani et al. |
| 6,837,892 B2 | 1/2005 | Shoham |
| 6,839,612 B2 | 1/2005 | Sanchez et al. |
| 6,856,826 B2 | 2/2005 | Seeley et al. |
| 6,856,827 B2 | 2/2005 | Seeley et al. |
| 6,879,880 B2 | 4/2005 | Nowlin et al. |
| 6,892,090 B2 | 5/2005 | Verard et al. |
| 6,920,347 B2 | 7/2005 | Simon et al. |
| 6,922,632 B2 | 7/2005 | Foxlin |
| 6,968,224 B2 | 11/2005 | Kessman et al. |
| 6,978,166 B2 | 12/2005 | Foley et al. |
| 6,988,009 B2 | 1/2006 | Grimm et al. |
| 6,991,627 B2 | 1/2006 | Madhani et al. |
| 6,996,487 B2 | 2/2006 | Jutras et al. |
| 6,999,852 B2 | 2/2006 | Green |
| 7,007,699 B2 | 3/2006 | Martinelli et al. |
| 7,016,457 B1 | 3/2006 | Senzig et al. |
| 7,043,961 B2 | 5/2006 | Pandey et al. |
| 7,062,006 B1 | 6/2006 | Pelc et al. |
| 7,063,705 B2 | 6/2006 | Young et al. |
| 7,072,707 B2 | 7/2006 | Galloway, Jr. et al. |
| 7,083,615 B2 | 8/2006 | Peterson et al. |
| 7,097,640 B2 | 8/2006 | Wang et al. |
| 7,099,428 B2 | 8/2006 | Clinthorne et al. |
| 7,108,421 B2 | 9/2006 | Gregerson et al. |
| 7,130,676 B2 | 10/2006 | Barrick |
| 7,139,418 B2 | 11/2006 | Abovitz et al. |
| 7,139,601 B2 | 11/2006 | Bucholz et al. |
| 7,155,316 B2 | 12/2006 | Sutherland et al. |
| 7,164,968 B2 | 1/2007 | Treat et al. |
| 7,167,738 B2 | 1/2007 | Schweikard et al. |
| 7,169,141 B2 | 1/2007 | Brock et al. |
| 7,172,627 B2 | 2/2007 | Fiere et al. |
| 7,194,120 B2 | 3/2007 | Wicker et al. |
| 7,197,107 B2 | 3/2007 | Arai et al. |
| 7,231,014 B2 | 6/2007 | Levy |
| 7,231,063 B2 | 6/2007 | Naimark et al. |
| 7,239,940 B2 | 7/2007 | Wang et al. |
| 7,248,914 B2 | 7/2007 | Hastings et al. |
| 7,301,648 B2 | 11/2007 | Foxlin |
| 7,302,288 B1 | 11/2007 | Schellenberg |
| 7,313,430 B2 | 12/2007 | Urquhart et al. |
| 7,318,805 B2 | 1/2008 | Schweikard et al. |
| 7,318,827 B2 | 1/2008 | Leitner et al. |
| 7,319,897 B2 | 1/2008 | Leitner et al. |
| 7,324,623 B2 | 1/2008 | Heuscher et al. |
| 7,327,865 B2 | 2/2008 | Fu et al. |
| 7,331,967 B2 | 2/2008 | Lee et al. |
| 7,333,642 B2 | 2/2008 | Green |
| 7,339,341 B2 | 3/2008 | Oleynikov et al. |
| 7,366,562 B2 | 4/2008 | Dukesherer et al. |
| 7,379,790 B2 | 5/2008 | Toth et al. |
| 7,386,365 B2 | 6/2008 | Nixon |
| 7,422,592 B2 | 9/2008 | Morley et al. |
| 7,435,216 B2 | 10/2008 | Kwon et al. |
| 7,440,793 B2 | 10/2008 | Chauhan et al. |
| 7,460,637 B2 | 12/2008 | Clinthorne et al. |
| 7,466,303 B2 | 12/2008 | Yi et al. |
| 7,493,153 B2 | 2/2009 | Ahmed et al. |
| 7,505,617 B2 | 3/2009 | Fu et al. |
| 7,533,892 B2 | 5/2009 | Schena et al. |
| 7,542,791 B2 | 6/2009 | Mire et al. |
| 7,555,331 B2 | 6/2009 | Viswanathan |
| 7,567,834 B2 | 7/2009 | Clayton et al. |
| 7,594,912 B2 | 9/2009 | Cooper et al. |
| 7,606,613 B2 | 10/2009 | Simon et al. |
| 7,607,440 B2 | 10/2009 | Coste-Maniere et al. |
| 7,623,902 B2 | 11/2009 | Pacheco |
| 7,630,752 B2 | 12/2009 | Viswanathan |
| 7,630,753 B2 | 12/2009 | Simon et al. |
| 7,643,862 B2 | 1/2010 | Schoenefeld |
| 7,660,623 B2 | 2/2010 | Hunter et al. |
| 7,661,881 B2 | 2/2010 | Gregerson et al. |
| 7,683,331 B2 | 3/2010 | Chang |
| 7,683,332 B2 | 3/2010 | Chang |
| 7,689,320 B2 | 3/2010 | Prisco et al. |
| 7,691,098 B2 | 4/2010 | Wallace et al. |
| 7,702,379 B2 | 4/2010 | Avinash et al. |
| 7,702,477 B2 | 4/2010 | Tuemmler et al. |
| 7,711,083 B2 | 5/2010 | Heigl et al. |
| 7,711,406 B2 | 5/2010 | Kuhn et al. |
| 7,720,523 B2 | 5/2010 | Omernick et al. |
| 7,725,253 B2 | 5/2010 | Foxlin |
| 7,726,171 B2 | 6/2010 | Langlotz et al. |
| 7,742,801 B2 | 6/2010 | Neubauer et al. |
| 7,751,865 B2 | 7/2010 | Jascob et al. |
| 7,760,849 B2 | 7/2010 | Zhang |
| 7,762,825 B2 | 7/2010 | Burbank et al. |
| 7,763,015 B2 | 7/2010 | Cooper et al. |
| 7,787,699 B2 | 8/2010 | Mahesh et al. |
| 7,796,728 B2 | 9/2010 | Bergfjord |
| 7,813,838 B2 | 10/2010 | Sommer |
| 7,818,044 B2 | 10/2010 | Dukesherer et al. |
| 7,819,859 B2 | 10/2010 | Prisco et al. |
| 7,824,401 B2 | 11/2010 | Manzo et al. |

(56) References Cited

U.S. PATENT DOCUMENTS

| | | |
|---|---|---|
| 7,831,294 B2 | 11/2010 | Viswanathan |
| 7,834,484 B2 | 11/2010 | Sartor |
| 7,835,557 B2 | 11/2010 | Kendrick et al. |
| 7,835,778 B2 | 11/2010 | Foley et al. |
| 7,835,784 B2 | 11/2010 | Mire et al. |
| 7,840,253 B2 | 11/2010 | Tremblay et al. |
| 7,840,256 B2 | 11/2010 | Lakin et al. |
| 7,843,158 B2 | 11/2010 | Prisco |
| 7,844,320 B2 | 11/2010 | Shahidi |
| 7,853,305 B2 | 12/2010 | Simon et al. |
| 7,853,313 B2 | 12/2010 | Thompson |
| 7,865,269 B2 | 1/2011 | Prisco et al. |
| D631,966 S | 2/2011 | Perloff et al. |
| 7,879,045 B2 | 2/2011 | Gielen et al. |
| 7,881,767 B2 | 2/2011 | Strommer et al. |
| 7,881,770 B2 | 2/2011 | Melkent et al. |
| 7,886,743 B2 | 2/2011 | Cooper et al. |
| RE42,194 E | 3/2011 | Foley et al. |
| RE42,226 E | 3/2011 | Foley et al. |
| 7,900,524 B2 | 3/2011 | Calloway et al. |
| 7,907,166 B2 | 3/2011 | Lamprecht et al. |
| 7,909,122 B2 | 3/2011 | Schena et al. |
| 7,925,653 B2 | 4/2011 | Saptharishi |
| 7,930,065 B2 | 4/2011 | Larkin et al. |
| 7,935,130 B2 | 5/2011 | Williams |
| 7,940,999 B2 | 5/2011 | Liao et al. |
| 7,945,012 B2 | 5/2011 | Ye et al. |
| 7,945,021 B2 | 5/2011 | Shapiro et al. |
| 7,953,470 B2 | 5/2011 | Vetter et al. |
| 7,954,397 B2 | 6/2011 | Choi et al. |
| 7,971,341 B2 | 7/2011 | Dukesherer et al. |
| 7,974,674 B2 | 7/2011 | Hauck et al. |
| 7,974,677 B2 | 7/2011 | Mire et al. |
| 7,974,681 B2 | 7/2011 | Wallace et al. |
| 7,979,157 B2 | 7/2011 | Anvari |
| 7,983,733 B2 | 7/2011 | Viswanathan |
| 7,988,215 B2 | 8/2011 | Seibold |
| 7,996,110 B2 | 8/2011 | Lipow et al. |
| 8,004,121 B2 | 8/2011 | Sartor |
| 8,004,229 B2 | 8/2011 | Nowlin et al. |
| 8,010,177 B2 | 8/2011 | Csavoy et al. |
| 8,019,045 B2 | 9/2011 | Kato |
| 8,021,310 B2 | 9/2011 | Sanborn et al. |
| 8,035,685 B2 | 10/2011 | Jensen |
| 8,046,054 B2 | 10/2011 | Kim et al. |
| 8,046,057 B2 | 10/2011 | Clarke |
| 8,052,688 B2 | 11/2011 | Wolf, II |
| 8,054,184 B2 | 11/2011 | Cline et al. |
| 8,054,752 B2 | 11/2011 | Druke et al. |
| 8,057,397 B2 | 11/2011 | Li et al. |
| 8,057,407 B2 | 11/2011 | Martinelli et al. |
| 8,062,288 B2 | 11/2011 | Cooper et al. |
| 8,062,375 B2 | 11/2011 | Glerum et al. |
| 8,066,524 B2 | 11/2011 | Burbank et al. |
| 8,073,335 B2 | 12/2011 | Labonville et al. |
| 8,079,950 B2 | 12/2011 | Stern et al. |
| 8,086,299 B2 | 12/2011 | Adler et al. |
| 8,092,370 B2 | 1/2012 | Roberts et al. |
| 8,098,914 B2 | 1/2012 | Liao et al. |
| 8,100,950 B2 | 1/2012 | St. Clair et al. |
| 8,105,320 B2 | 1/2012 | Manzo |
| 8,108,025 B2 | 1/2012 | Csavoy et al. |
| 8,109,877 B2 | 2/2012 | Moctezuma de la Barrera et al. |
| 8,112,292 B2 | 2/2012 | Simon |
| 8,116,430 B1 | 2/2012 | Shapiro et al. |
| 8,120,301 B2 | 2/2012 | Goldberg et al. |
| 8,121,249 B2 | 2/2012 | Wang et al. |
| 8,123,675 B2 | 2/2012 | Funda et al. |
| 8,133,229 B1 | 3/2012 | Bonutti |
| 8,142,420 B2 | 3/2012 | Schena |
| 8,147,494 B2 | 4/2012 | Leitner et al. |
| 8,150,494 B2 | 4/2012 | Simon et al. |
| 8,150,497 B2 | 4/2012 | Gielen et al. |
| 8,150,498 B2 | 4/2012 | Gielen et al. |
| 8,165,658 B2 | 4/2012 | Waynik et al. |
| 8,170,313 B2 | 5/2012 | Kendrick et al. |
| 8,179,073 B2 | 5/2012 | Farritor et al. |
| 8,182,476 B2 | 5/2012 | Julian et al. |
| 8,184,880 B2 | 5/2012 | Zhao et al. |
| 8,202,278 B2 | 6/2012 | Orban, III et al. |
| 8,208,708 B2 | 6/2012 | Homan et al. |
| 8,208,988 B2 | 6/2012 | Jenser |
| 8,219,177 B2 | 7/2012 | Smith et al. |
| 8,219,178 B2 | 7/2012 | Smith et al. |
| 8,220,468 B2 | 7/2012 | Cooper et al. |
| 8,224,024 B2 | 7/2012 | Foxlin et al. |
| 8,224,484 B2 | 7/2012 | Swarup et al. |
| 8,225,798 B2 | 7/2012 | Baldwin et al. |
| 8,228,368 B2 | 7/2012 | Zhao et al. |
| 8,231,610 B2 | 7/2012 | Jo et al. |
| 8,239,001 B2 | 8/2012 | Verard et al. |
| 8,241,271 B2 | 8/2012 | Millman et al. |
| 8,248,413 B2 | 8/2012 | Gattani et al. |
| 8,256,319 B2 | 9/2012 | Cooper et al. |
| 8,263,933 B2 | 9/2012 | Zeile et al. |
| 8,271,069 B2 | 9/2012 | Jascob et al. |
| 8,271,130 B2 | 9/2012 | Hourtash |
| 8,281,670 B2 | 10/2012 | Larkin et al. |
| 8,282,653 B2 | 10/2012 | Nelson et al. |
| 8,301,226 B2 | 10/2012 | Csavoy et al. |
| 8,311,611 B2 | 11/2012 | Csavoy et al. |
| 8,320,991 B2 | 11/2012 | Jascob et al. |
| 8,332,012 B2 | 12/2012 | Kienzle, III |
| 8,333,755 B2 | 12/2012 | Cooper et al. |
| 8,335,552 B2 | 12/2012 | Stiles |
| 8,335,557 B2 | 12/2012 | Maschke |
| 8,348,931 B2 | 1/2013 | Cooper et al. |
| 8,353,963 B2 | 1/2013 | Glerum |
| 8,358,818 B2 | 1/2013 | Miga et al. |
| 8,359,730 B2 | 1/2013 | Burg et al. |
| 8,374,673 B2 | 2/2013 | Adcox et al. |
| 8,374,723 B2 | 2/2013 | Zhao et al. |
| 8,379,791 B2 | 2/2013 | Forthmann et al. |
| 8,386,019 B2 | 2/2013 | Camus et al. |
| 8,392,022 B2 | 3/2013 | Ortmaier et al. |
| 8,394,099 B2 | 3/2013 | Patwardhan |
| 8,395,342 B2 | 3/2013 | Prisco |
| 8,398,634 B2 | 3/2013 | Manzo et al. |
| 8,400,094 B2 | 3/2013 | Schena |
| 8,414,957 B2 | 4/2013 | Enzerink et al. |
| 8,418,073 B2 | 4/2013 | Mohr et al. |
| 8,442,619 B2 * | 5/2013 | Li .................. G16H 50/50 600/407 |
| 8,450,694 B2 | 5/2013 | Baviera et al. |
| 8,452,447 B2 | 5/2013 | Nixon |
| RE44,305 E | 6/2013 | Foley et al. |
| 8,462,911 B2 | 6/2013 | Vesel et al. |
| 8,465,476 B2 | 6/2013 | Rogers et al. |
| 8,465,771 B2 | 6/2013 | Wan et al. |
| 8,467,851 B2 | 6/2013 | Mire et al. |
| 8,467,852 B2 | 6/2013 | Csavoy et al. |
| 8,469,947 B2 | 6/2013 | Devengenzo et al. |
| RE44,392 E | 7/2013 | Hynes |
| 8,483,434 B2 | 7/2013 | Buehner et al. |
| 8,483,800 B2 | 7/2013 | Jensen et al. |
| 8,486,532 B2 | 7/2013 | Enzerink et al. |
| 8,489,235 B2 | 7/2013 | Moll et al. |
| 8,500,722 B2 | 8/2013 | Cooper |
| 8,500,728 B2 | 8/2013 | Newton et al. |
| 8,504,201 B2 | 8/2013 | Moll et al. |
| 8,506,555 B2 | 8/2013 | Ruiz Morales |
| 8,506,556 B2 | 8/2013 | Schena |
| 8,508,173 B2 | 8/2013 | Goldberg et al. |
| 8,512,318 B2 | 8/2013 | Tovey et al. |
| 8,515,576 B2 | 8/2013 | Lipow et al. |
| 8,518,120 B2 | 8/2013 | Glerum et al. |
| 8,521,331 B2 | 8/2013 | Itkowitz |
| 8,526,688 B2 | 9/2013 | Groszmann et al. |
| 8,526,700 B2 | 9/2013 | Isaacs |
| 8,527,094 B2 | 9/2013 | Kumar et al. |
| 8,528,440 B2 | 9/2013 | Morley et al. |
| 8,532,741 B2 | 9/2013 | Heruth et al. |
| 8,541,970 B2 | 9/2013 | Nowlin et al. |
| 8,548,563 B2 | 10/2013 | Simon et al. |

(56) References Cited

U.S. PATENT DOCUMENTS

| | | |
|---|---|---|
| 8,549,732 B2 | 10/2013 | Burg et al. |
| 8,551,114 B2 | 10/2013 | Ramos de la Pena |
| 8,551,116 B2 | 10/2013 | Julian et al. |
| 8,556,807 B2 | 10/2013 | Scott et al. |
| 8,556,979 B2 | 10/2013 | Glerum et al. |
| 8,560,118 B2 | 10/2013 | Green et al. |
| 8,561,473 B2 | 10/2013 | Blumenkranz |
| 8,562,594 B2 | 10/2013 | Cooper et al. |
| 8,571,638 B2 | 10/2013 | Shoham |
| 8,571,710 B2 | 10/2013 | Coste-Maniere et al. |
| 8,573,465 B2 | 11/2013 | Shelton, IV |
| 8,574,303 B2 | 11/2013 | Sharkey et al. |
| 8,585,420 B2 | 11/2013 | Burbank et al. |
| 8,594,841 B2 | 11/2013 | Zhao et al. |
| 8,597,198 B2 | 12/2013 | Sanborn et al. |
| 8,600,478 B2 | 12/2013 | Verard et al. |
| 8,603,077 B2 | 12/2013 | Cooper et al. |
| 8,611,985 B2 | 12/2013 | Lavallee et al. |
| 8,613,230 B2 | 12/2013 | Blumenkranz et al. |
| 8,621,939 B2 | 1/2014 | Blumenkranz et al. |
| 8,624,537 B2 | 1/2014 | Nowlin et al. |
| 8,630,389 B2 | 1/2014 | Kato |
| 8,634,897 B2 | 1/2014 | Simon et al. |
| 8,634,957 B2 | 1/2014 | Toth et al. |
| 8,638,056 B2 | 1/2014 | Goldberg et al. |
| 8,638,057 B2 | 1/2014 | Goldberg et al. |
| 8,639,000 B2 | 1/2014 | Zhao et al. |
| 8,641,726 B2 | 2/2014 | Bonutti |
| 8,644,907 B2 | 2/2014 | Hartmann et al. |
| 8,657,809 B2 | 2/2014 | Schoepp |
| 8,660,635 B2 | 2/2014 | Simon et al. |
| 8,666,544 B2 | 3/2014 | Moll et al. |
| 8,675,939 B2 | 3/2014 | Moctezuma de la Barrera |
| 8,678,647 B2 | 3/2014 | Gregerson et al. |
| 8,679,125 B2 | 3/2014 | Smith et al. |
| 8,679,183 B2 | 3/2014 | Glerum et al. |
| 8,682,413 B2 | 3/2014 | Lloyd |
| 8,684,253 B2 | 4/2014 | Giordano et al. |
| 8,685,098 B2 | 4/2014 | Glerum et al. |
| 8,693,730 B2 | 4/2014 | Umasuthan et al. |
| 8,694,075 B2 | 4/2014 | Groszmann et al. |
| 8,696,458 B2 | 4/2014 | Foxlin et al. |
| 8,700,123 B2 | 4/2014 | Okamura et al. |
| 8,706,086 B2 | 4/2014 | Glerum |
| 8,706,185 B2 | 4/2014 | Foley et al. |
| 8,706,301 B2 | 4/2014 | Zhao et al. |
| 8,717,430 B2 | 5/2014 | Simon et al. |
| 8,727,618 B2 | 5/2014 | Maschke et al. |
| 8,734,432 B2 | 5/2014 | Tuma et al. |
| 8,738,115 B2 | 5/2014 | Amberg et al. |
| 8,738,181 B2 | 5/2014 | Greer et al. |
| 8,740,882 B2 | 6/2014 | Jun et al. |
| 8,746,252 B2 | 6/2014 | McGrogan et al. |
| 8,749,189 B2 | 6/2014 | Nowlin et al. |
| 8,749,190 B2 | 6/2014 | Nowlin et al. |
| 8,761,930 B2 | 6/2014 | Nixon |
| 8,764,448 B2 | 7/2014 | Yang et al. |
| 8,771,170 B2 | 7/2014 | Mesallum et al. |
| 8,781,186 B2 | 7/2014 | Clements et al. |
| 8,781,630 B2 | 7/2014 | Banks et al. |
| 8,784,385 B2 | 7/2014 | Boyden et al. |
| 8,786,241 B2 | 7/2014 | Nowlin et al. |
| 8,787,520 B2 | 7/2014 | Baba |
| 8,792,704 B2 | 7/2014 | Isaacs |
| 8,798,231 B2 | 8/2014 | Notohara et al. |
| 8,800,838 B2 | 8/2014 | Shelton, IV |
| 8,808,164 B2 | 8/2014 | Hoffman et al. |
| 8,812,077 B2 | 8/2014 | Dempsey |
| 8,814,793 B2 | 8/2014 | Brabrand |
| 8,816,628 B2 | 8/2014 | Nowlin et al. |
| 8,818,105 B2 | 8/2014 | Myronenko et al. |
| 8,820,605 B2 | 9/2014 | Shelton, IV |
| 8,821,511 B2 | 9/2014 | Von Jako et al. |
| 8,823,308 B2 | 9/2014 | Nowlin et al. |
| 8,827,996 B2 | 9/2014 | Scott et al. |
| 8,828,024 B2 | 9/2014 | Farritor et al. |
| 8,830,224 B2 | 9/2014 | Zhao et al. |
| 8,834,489 B2 | 9/2014 | Cooper et al. |
| 8,834,490 B2 | 9/2014 | Bonutti |
| 8,838,270 B2 | 9/2014 | Druke et al. |
| 8,844,789 B2 | 9/2014 | Shelton, IV et al. |
| 8,855,822 B2 | 10/2014 | Bartol et al. |
| 8,858,598 B2 | 10/2014 | Seifert et al. |
| 8,860,753 B2 | 10/2014 | Bhandarkar et al. |
| 8,864,751 B2 | 10/2014 | Prisco et al. |
| 8,864,798 B2 | 10/2014 | Weiman et al. |
| 8,864,833 B2 | 10/2014 | Glerum et al. |
| 8,867,703 B2 | 10/2014 | Shapiro et al. |
| 8,870,880 B2 | 10/2014 | Himmelberger et al. |
| 8,876,866 B2 | 11/2014 | Zappacosta et al. |
| 8,880,223 B2 | 11/2014 | Raj et al. |
| 8,882,803 B2 | 11/2014 | Iott et al. |
| 8,883,210 B1 | 11/2014 | Truncale et al. |
| 8,888,821 B2 | 11/2014 | Rezach et al. |
| 8,888,853 B2 | 11/2014 | Glerum et al. |
| 8,888,854 B2 | 11/2014 | Glerum et al. |
| 8,894,652 B2 | 11/2014 | Seifert et al. |
| 8,894,688 B2 | 11/2014 | Suh |
| 8,894,691 B2 | 11/2014 | Iott et al. |
| 8,906,069 B2 | 12/2014 | Hansell et al. |
| 8,964,934 B2 | 2/2015 | Ein-Gal |
| 8,992,580 B2 | 3/2015 | Bar et al. |
| 8,996,169 B2 | 3/2015 | Lightcap et al. |
| 9,001,963 B2 | 4/2015 | Sowards-Emmerd et al. |
| 9,002,076 B2 | 4/2015 | Khadem et al. |
| 9,044,190 B2 | 6/2015 | Rubner et al. |
| 9,107,683 B2 | 8/2015 | Hourtash et al. |
| 9,125,556 B2 | 9/2015 | Zehavi et al. |
| 9,131,986 B2 | 9/2015 | Greer et al. |
| 9,215,968 B2 | 12/2015 | Schostek et al. |
| 9,308,050 B2 | 4/2016 | Kostrzewski et al. |
| 9,380,984 B2 | 7/2016 | Li et al. |
| 9,393,039 B2 | 7/2016 | Lechner et al. |
| 9,398,886 B2 | 7/2016 | Gregerson et al. |
| 9,398,890 B2 | 7/2016 | Dong et al. |
| 9,414,859 B2 | 8/2016 | Ballard et al. |
| 9,420,975 B2 | 8/2016 | Gutfleisch et al. |
| 9,492,235 B2 | 11/2016 | Hourtash et al. |
| 9,592,096 B2 | 3/2017 | Maillet et al. |
| 9,750,465 B2 | 9/2017 | Engel et al. |
| 9,757,203 B2 | 9/2017 | Hourtash et al. |
| 9,795,354 B2 | 10/2017 | Menegaz et al. |
| 9,814,535 B2 | 11/2017 | Bar et al. |
| 9,820,783 B2 | 11/2017 | Donner et al. |
| 9,833,265 B2 | 12/2017 | Donner et al. |
| 9,848,922 B2 | 12/2017 | Tohmeh et al. |
| 9,925,011 B2 | 3/2018 | Gombert et al. |
| 9,931,025 B1 | 4/2018 | Graetzel et al. |
| 10,034,717 B2 | 7/2018 | Miller et al. |
| 2001/0036302 A1 | 11/2001 | Miller |
| 2002/0035321 A1 | 3/2002 | Bucholz et al. |
| 2004/0068172 A1 | 4/2004 | Nowinski et al. |
| 2004/0076259 A1 | 4/2004 | Jensen et al. |
| 2005/0096502 A1 | 5/2005 | Khalili |
| 2005/0143651 A1 | 6/2005 | Verard et al. |
| 2005/0171558 A1 | 8/2005 | Abovitz et al. |
| 2006/0100610 A1 | 5/2006 | Wallace et al. |
| 2006/0173329 A1 | 8/2006 | Marquart et al. |
| 2006/0184396 A1 | 8/2006 | Dennis et al. |
| 2006/0241416 A1 | 10/2006 | Marquart et al. |
| 2006/0291612 A1 | 12/2006 | Nishide et al. |
| 2007/0015987 A1 | 1/2007 | Benlloch Baviera et al. |
| 2007/0021738 A1 | 1/2007 | Hasser et al. |
| 2007/0038059 A1 | 2/2007 | Sheffer et al. |
| 2007/0073133 A1 | 3/2007 | Schoenefeld |
| 2007/0073137 A1* | 3/2007 | Schoenefeld .......... A61B 5/064 600/407 |
| 2007/0156121 A1 | 7/2007 | Millman et al. |
| 2007/0156157 A1 | 7/2007 | Nahum et al. |
| 2007/0167712 A1 | 7/2007 | Keglovich et al. |
| 2007/0233238 A1 | 10/2007 | Huynh et al. |
| 2008/0004523 A1 | 1/2008 | Jensen |
| 2008/0013809 A1 | 1/2008 | Zhu et al. |
| 2008/0033283 A1 | 2/2008 | Dellaca et al. |

(56) References Cited

U.S. PATENT DOCUMENTS

| | | |
|---|---|---|
| 2008/0046122 A1 | 2/2008 | Manzo et al. |
| 2008/0082109 A1 | 4/2008 | Moll et al. |
| 2008/0108912 A1 | 5/2008 | Node-Langlois |
| 2008/0108991 A1 | 5/2008 | Von Jako |
| 2008/0109012 A1 | 5/2008 | Falco et al. |
| 2008/0144906 A1 | 6/2008 | Allred et al. |
| 2008/0161680 A1 | 7/2008 | Von Jako et al. |
| 2008/0161682 A1 | 7/2008 | Kendrick et al. |
| 2008/0177203 A1 | 7/2008 | von Jako |
| 2008/0214922 A1 | 9/2008 | Hartmann et al. |
| 2008/0228068 A1 | 9/2008 | Viswanathan et al. |
| 2008/0228196 A1 | 9/2008 | Wang et al. |
| 2008/0235052 A1 | 9/2008 | Node-Langlois et al. |
| 2008/0269596 A1 | 10/2008 | Revie et al. |
| 2008/0287771 A1 | 11/2008 | Anderson |
| 2008/0287781 A1 | 11/2008 | Revie et al. |
| 2008/0300477 A1 | 12/2008 | Lloyd et al. |
| 2008/0300478 A1 | 12/2008 | Zuhars et al. |
| 2008/0302950 A1 | 12/2008 | Park et al. |
| 2008/0306490 A1 | 12/2008 | Lakin et al. |
| 2008/0319311 A1 | 12/2008 | Hamadeh |
| 2009/0012509 A1 | 1/2009 | Csavoy et al. |
| 2009/0030428 A1 | 1/2009 | Omori et al. |
| 2009/0080737 A1 | 3/2009 | Battle et al. |
| 2009/0185655 A1 | 7/2009 | Koken et al. |
| 2009/0198121 A1 | 8/2009 | Hoheisel |
| 2009/0216113 A1 | 8/2009 | Meier et al. |
| 2009/0228019 A1 | 9/2009 | Gross et al. |
| 2009/0259123 A1 | 10/2009 | Navab et al. |
| 2009/0259230 A1 | 10/2009 | Khadem et al. |
| 2009/0264899 A1 | 10/2009 | Appenrodt et al. |
| 2009/0281417 A1 | 11/2009 | Hartmann et al. |
| 2010/0022874 A1 | 1/2010 | Wang et al. |
| 2010/0039506 A1 | 2/2010 | Sarvestani et al. |
| 2010/0125286 A1 | 5/2010 | Wang et al. |
| 2010/0130986 A1 | 5/2010 | Mailloux et al. |
| 2010/0228117 A1 | 9/2010 | Hartmann |
| 2010/0228265 A1 | 9/2010 | Prisco |
| 2010/0249571 A1 | 9/2010 | Jensen et al. |
| 2010/0274120 A1 | 10/2010 | Heuscher |
| 2010/0280363 A1 | 11/2010 | Skarda et al. |
| 2010/0331858 A1 | 12/2010 | Simaan et al. |
| 2011/0022229 A1 | 1/2011 | Jang et al. |
| 2011/0077504 A1 | 3/2011 | Fischer et al. |
| 2011/0098553 A1 | 4/2011 | Robbins et al. |
| 2011/0137152 A1 | 6/2011 | Li |
| 2011/0213384 A1 | 9/2011 | Jeong |
| 2011/0224684 A1 | 9/2011 | Larkin et al. |
| 2011/0224685 A1 | 9/2011 | Larkin et al. |
| 2011/0224686 A1 | 9/2011 | Larkin et al. |
| 2011/0224687 A1 | 9/2011 | Larkin et al. |
| 2011/0224688 A1 | 9/2011 | Larkin et al. |
| 2011/0224689 A1 | 9/2011 | Larkin et al. |
| 2011/0224825 A1 | 9/2011 | Larkin et al. |
| 2011/0230967 A1 | 9/2011 | O'Halloran et al. |
| 2011/0238080 A1 | 9/2011 | Ranjit et al. |
| 2011/0276058 A1 | 11/2011 | Choi et al. |
| 2011/0282189 A1 | 11/2011 | Graumann |
| 2011/0286573 A1 | 11/2011 | Schretter et al. |
| 2011/0295062 A1 | 12/2011 | Gratacos Solsona et al. |
| 2011/0295370 A1 | 12/2011 | Suh et al. |
| 2011/0306986 A1* | 12/2011 | Lee .................. A61B 34/37 606/130 |
| 2012/0035507 A1 | 2/2012 | George et al. |
| 2012/0046668 A1 | 2/2012 | Gantes |
| 2012/0051498 A1 | 3/2012 | Koishi |
| 2012/0053597 A1 | 3/2012 | Anvari et al. |
| 2012/0059248 A1 | 3/2012 | Holsing et al. |
| 2012/0071753 A1 | 3/2012 | Hunter et al. |
| 2012/0108954 A1 | 5/2012 | Schulhauser et al. |
| 2012/0136372 A1 | 5/2012 | Amat Girbau et al. |
| 2012/0143084 A1 | 6/2012 | Shoham |
| 2012/0184839 A1 | 7/2012 | Woerlein |
| 2012/0197182 A1 | 8/2012 | Millman et al. |
| 2012/0226145 A1 | 9/2012 | Chang et al. |
| 2012/0235909 A1 | 9/2012 | Birkenbach et al. |
| 2012/0245596 A1 | 9/2012 | Meenink |
| 2012/0253332 A1 | 10/2012 | Moll |
| 2012/0253360 A1 | 10/2012 | White et al. |
| 2012/0256092 A1 | 10/2012 | Zingerman |
| 2012/0294498 A1 | 11/2012 | Popovic |
| 2012/0296203 A1 | 11/2012 | Hartmann et al. |
| 2013/0006267 A1 | 1/2013 | Odermatt et al. |
| 2013/0016889 A1 | 1/2013 | Myronenko et al. |
| 2013/0030571 A1 | 1/2013 | Ruiz Morales et al. |
| 2013/0035583 A1 | 2/2013 | Park et al. |
| 2013/0060146 A1 | 3/2013 | Yang et al. |
| 2013/0060337 A1 | 3/2013 | Petersheim et al. |
| 2013/0094742 A1 | 4/2013 | Feilkas |
| 2013/0096574 A1 | 4/2013 | Kang et al. |
| 2013/0113791 A1 | 5/2013 | Isaacs et al. |
| 2013/0116706 A1 | 5/2013 | Lee et al. |
| 2013/0131695 A1 | 5/2013 | Scarfogliero et al. |
| 2013/0144307 A1 | 6/2013 | Jeong et al. |
| 2013/0158542 A1 | 6/2013 | Manzo et al. |
| 2013/0165937 A1 | 6/2013 | Patwardhan |
| 2013/0178867 A1 | 7/2013 | Farritor et al. |
| 2013/0178868 A1 | 7/2013 | Roh |
| 2013/0178870 A1 | 7/2013 | Schena |
| 2013/0204271 A1 | 8/2013 | Brisson et al. |
| 2013/0211419 A1 | 8/2013 | Jensen |
| 2013/0211420 A1 | 8/2013 | Jensen |
| 2013/0218142 A1 | 8/2013 | Tuma et al. |
| 2013/0223702 A1 | 8/2013 | Holsing et al. |
| 2013/0225942 A1 | 8/2013 | Holsing et al. |
| 2013/0225943 A1 | 8/2013 | Holsing et al. |
| 2013/0231556 A1 | 9/2013 | Holsing et al. |
| 2013/0237995 A1 | 9/2013 | Lee et al. |
| 2013/0245375 A1 | 9/2013 | DiMaio et al. |
| 2013/0261640 A1 | 10/2013 | Kim et al. |
| 2013/0272488 A1 | 10/2013 | Bailey et al. |
| 2013/0272489 A1 | 10/2013 | Dickman et al. |
| 2013/0274761 A1 | 10/2013 | Devengenzo et al. |
| 2013/0281821 A1 | 10/2013 | Liu et al. |
| 2013/0296884 A1 | 11/2013 | Taylor et al. |
| 2013/0303887 A1 | 11/2013 | Holsing et al. |
| 2013/0307955 A1 | 11/2013 | Deitz et al. |
| 2013/0317521 A1 | 11/2013 | Choi et al. |
| 2013/0325033 A1 | 12/2013 | Schena et al. |
| 2013/0325035 A1 | 12/2013 | Hauck et al. |
| 2013/0331686 A1 | 12/2013 | Freysinger et al. |
| 2013/0331858 A1 | 12/2013 | Devengenzo et al. |
| 2013/0331861 A1 | 12/2013 | Yoon |
| 2013/0342578 A1 | 12/2013 | Isaacs |
| 2013/0345717 A1 | 12/2013 | Markvicka et al. |
| 2013/0345757 A1 | 12/2013 | Stad |
| 2014/0001235 A1 | 1/2014 | Shelton, IV |
| 2014/0012131 A1 | 1/2014 | Heruth et al. |
| 2014/0031664 A1 | 1/2014 | Kang et al. |
| 2014/0046128 A1 | 2/2014 | Lee et al. |
| 2014/0046132 A1 | 2/2014 | Hoeg et al. |
| 2014/0046340 A1 | 2/2014 | Wilson et al. |
| 2014/0049629 A1 | 2/2014 | Siewerdsen et al. |
| 2014/0058406 A1 | 2/2014 | Tsekos |
| 2014/0073914 A1 | 3/2014 | Lavallee et al. |
| 2014/0080086 A1 | 3/2014 | Chen |
| 2014/0081128 A1 | 3/2014 | Verard et al. |
| 2014/0088612 A1 | 3/2014 | Bartol et al. |
| 2014/0094694 A1 | 4/2014 | Moctezuma de la Barrera |
| 2014/0094851 A1 | 4/2014 | Gordon |
| 2014/0096369 A1 | 4/2014 | Matsumoto et al. |
| 2014/0100587 A1 | 4/2014 | Farritor et al. |
| 2014/0121676 A1 | 5/2014 | Kostrzewski et al. |
| 2014/0128882 A1 | 5/2014 | Kwak et al. |
| 2014/0130810 A1 | 5/2014 | Azizian et al. |
| 2014/0135796 A1 | 5/2014 | Simon et al. |
| 2014/0142591 A1 | 5/2014 | Alvarez et al. |
| 2014/0142592 A1 | 5/2014 | Moon et al. |
| 2014/0148692 A1 | 5/2014 | Hartmann et al. |
| 2014/0163581 A1 | 6/2014 | Devengenzo et al. |
| 2014/0171781 A1 | 6/2014 | Stiles |
| 2014/0171900 A1 | 6/2014 | Stiles |
| 2014/0171965 A1 | 6/2014 | Loh et al. |
| 2014/0180308 A1 | 6/2014 | von Grunberg |

(56) References Cited

U.S. PATENT DOCUMENTS

| | | |
|---|---|---|
| 2014/0180309 A1 | 6/2014 | Seeber et al. |
| 2014/0187915 A1 | 7/2014 | Yaroshenko et al. |
| 2014/0188132 A1 | 7/2014 | Kang |
| 2014/0194699 A1 | 7/2014 | Roh et al. |
| 2014/0221819 A1 | 8/2014 | Sarment |
| 2014/0222023 A1 | 8/2014 | Kim et al. |
| 2014/0228631 A1 | 8/2014 | Kwak et al. |
| 2014/0234804 A1 | 8/2014 | Huang et al. |
| 2014/0257328 A1 | 9/2014 | Kim et al. |
| 2014/0257329 A1 | 9/2014 | Jang et al. |
| 2014/0257330 A1 | 9/2014 | Choi et al. |
| 2014/0275760 A1 | 9/2014 | Lee et al. |
| 2014/0275985 A1 | 9/2014 | Walker et al. |
| 2014/0276931 A1 | 9/2014 | Parihar et al. |
| 2014/0276940 A1 | 9/2014 | Seo |
| 2014/0276944 A1 | 9/2014 | Farritor et al. |
| 2014/0288413 A1 | 9/2014 | Hwang et al. |
| 2014/0299648 A1 | 10/2014 | Shelton, IV et al. |
| 2014/0303434 A1 | 10/2014 | Farritor et al. |
| 2014/0303643 A1 | 10/2014 | Ha et al. |
| 2014/0305995 A1 | 10/2014 | Shelton, IV et al. |
| 2014/0309659 A1 | 10/2014 | Roh et al. |
| 2014/0316436 A1 | 10/2014 | Bar et al. |
| 2014/0323803 A1 | 10/2014 | Hoffman et al. |
| 2014/0324070 A1 | 10/2014 | Min et al. |
| 2014/0330288 A1 | 11/2014 | Date et al. |
| 2014/0364720 A1 | 12/2014 | Darrow et al. |
| 2014/0371577 A1 | 12/2014 | Maillet et al. |
| 2015/0039034 A1 | 2/2015 | Frankel et al. |
| 2015/0085970 A1 | 3/2015 | Bouhnik et al. |
| 2015/0146847 A1 | 5/2015 | Liu |
| 2015/0150524 A1 | 6/2015 | Yorkston et al. |
| 2015/0196261 A1 | 7/2015 | Funk |
| 2015/0213633 A1 | 7/2015 | Chang et al. |
| 2015/0335480 A1 | 11/2015 | Alvarez et al. |
| 2015/0342647 A1 | 12/2015 | Frankel et al. |
| 2016/0005194 A1 | 1/2016 | Schretter et al. |
| 2016/0166329 A1 | 6/2016 | Langan et al. |
| 2016/0235480 A1 | 8/2016 | Scholl et al. |
| 2016/0249990 A1 | 9/2016 | Glozman et al. |
| 2016/0302871 A1 | 10/2016 | Gregerson et al. |
| 2016/0320322 A1 | 11/2016 | Suzuki |
| 2016/0331335 A1 | 11/2016 | Gregerson et al. |
| 2017/0135770 A1 | 5/2017 | Scholl et al. |
| 2017/0143284 A1 | 5/2017 | Sehnert et al. |
| 2017/0143426 A1 | 5/2017 | Isaacs et al. |
| 2017/0156816 A1 | 6/2017 | Ibrahim |
| 2017/0202629 A1 | 7/2017 | Maillet et al. |
| 2017/0212723 A1 | 7/2017 | Atarot et al. |
| 2017/0215825 A1 | 8/2017 | Johnson et al. |
| 2017/0215826 A1 | 8/2017 | Johnson et al. |
| 2017/0215827 A1 | 8/2017 | Johnson et al. |
| 2017/0231710 A1 | 8/2017 | Scholl et al. |
| 2017/0258426 A1 | 9/2017 | Risher-Kelly et al. |
| 2017/0273748 A1 | 9/2017 | Hourtash et al. |
| 2017/0296277 A1 | 10/2017 | Hourtash et al. |
| 2017/0360493 A1 | 12/2017 | Zucher et al. |
| 2020/0120308 A1* | 4/2020 | McMillan ............... G06F 3/017 |

\* cited by examiner

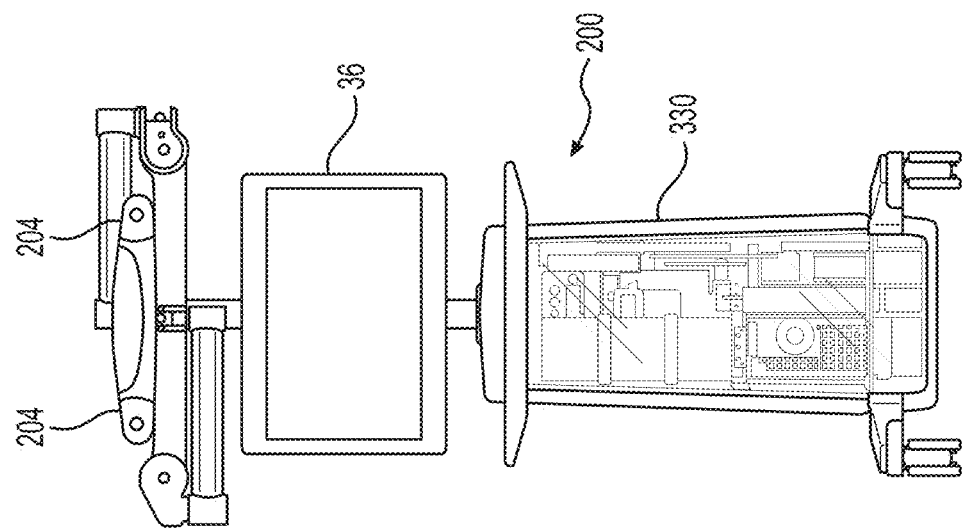
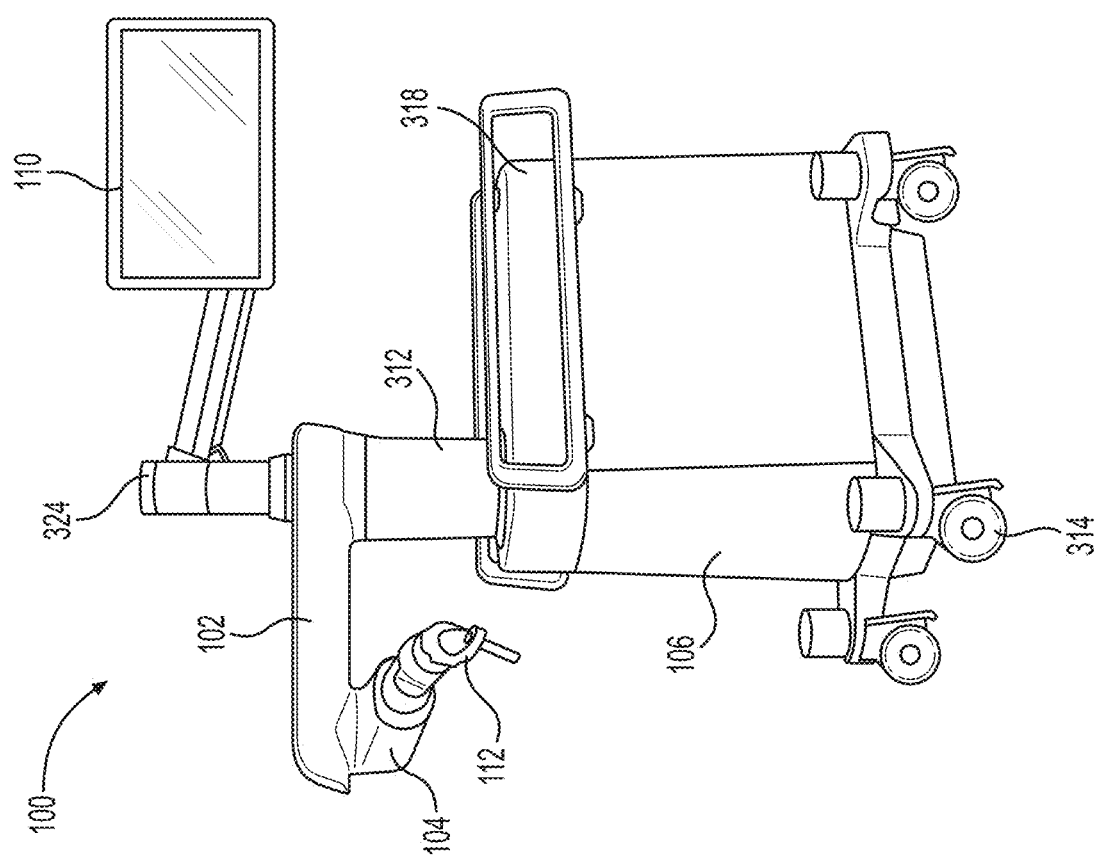
FIG. 3

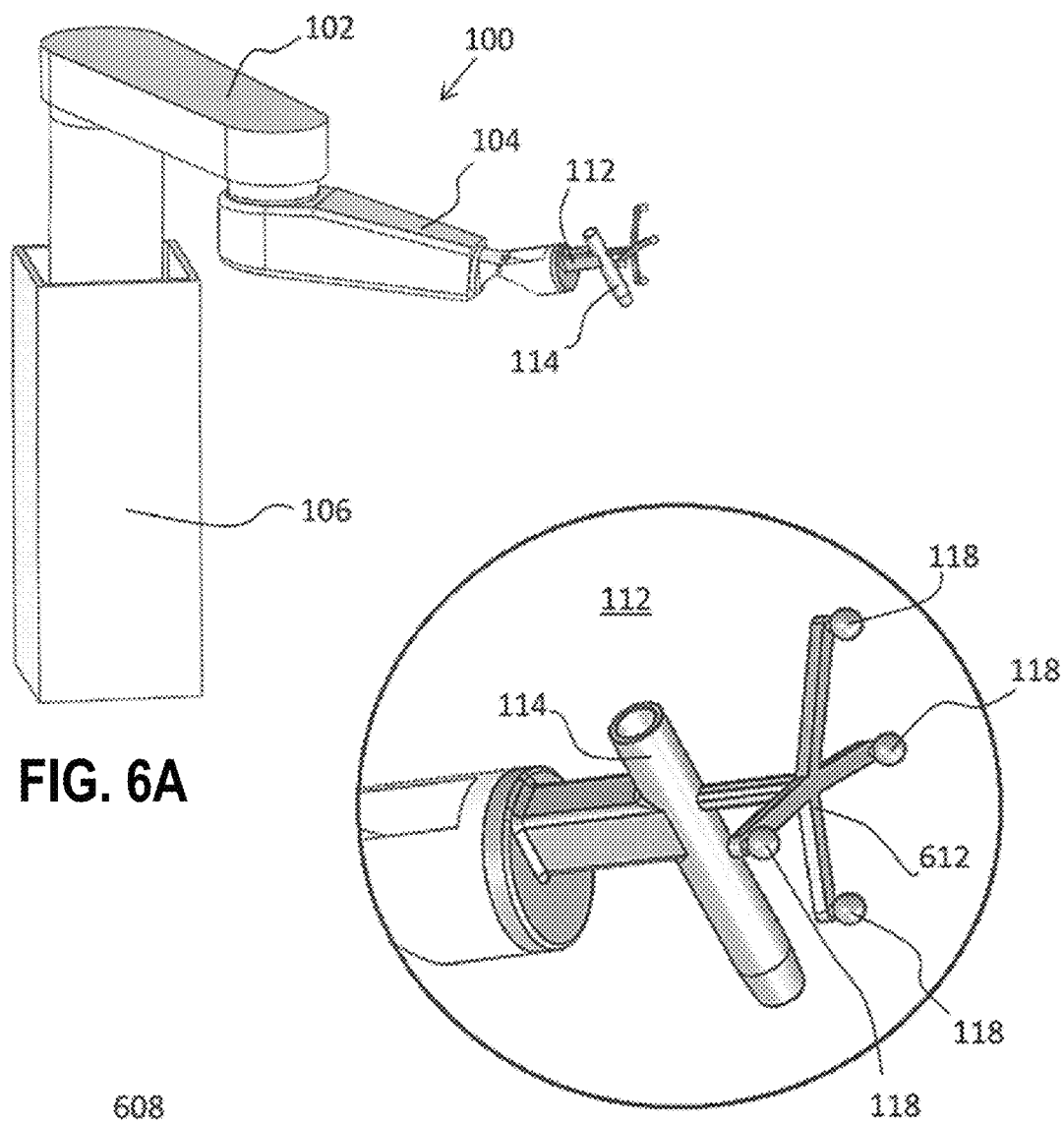
FIG. 6A
FIG. 6B
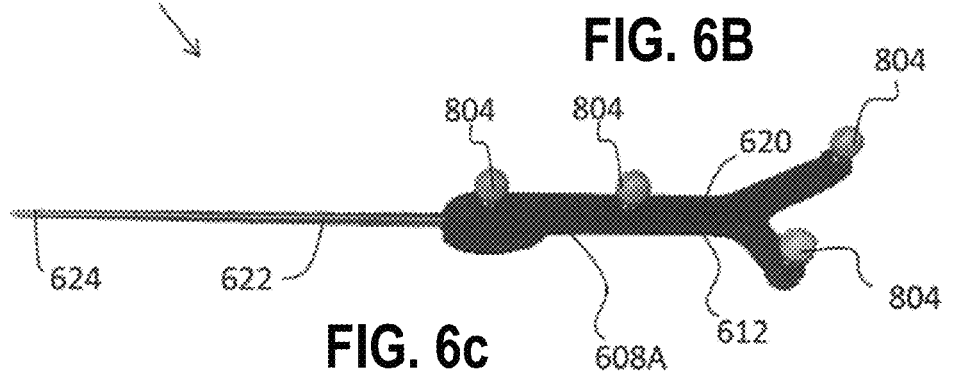
FIG. 6c

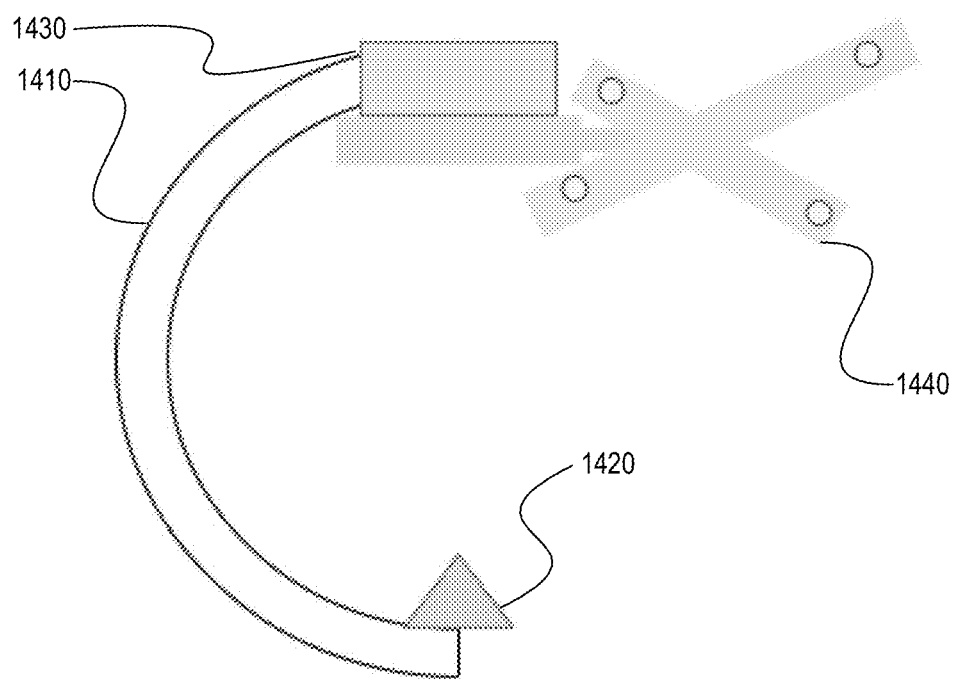
FIG. 14
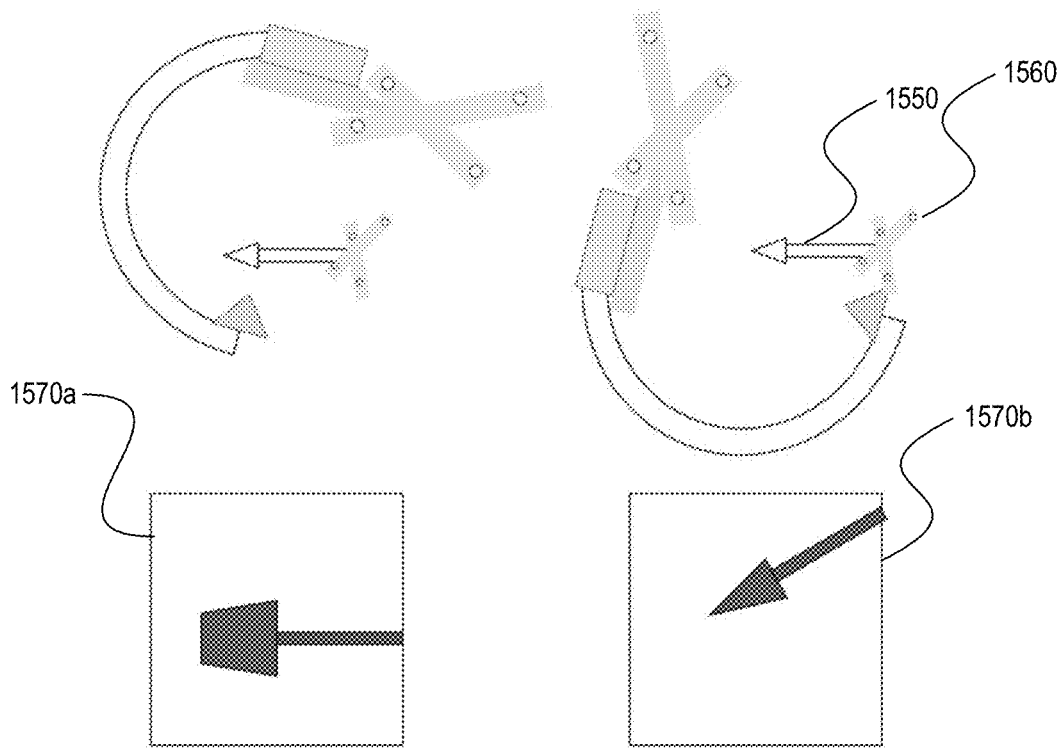
FIG. 15A  FIG. 15B

ACCURACY CHECK AND AUTOMATIC CALIBRATION OF TRACKED INSTRUMENTS

FIELD

The present disclosure relates to medical devices and systems, and more particularly, checking accuracy and performing automatic calibration of tracked instruments in a camera tracking systems used for computer assisted navigation during surgery.

BACKGROUND

Surgical operating rooms can contain a diverse range of medical equipment, which can include computer assisted surgical navigation systems, medical imaging devices (e.g., computerized tomography ("CT") scanners, fluoroscopy imaging, etc.), and surgical robots.

A computer assisted surgical navigation system can provide a surgeon with computerized visualization of the present pose of a surgical tool relative to medical images of a patient's anatomy. Camera tracking systems for computer assisted surgical navigation typically use a set of cameras to track pose of a reference array on a surgical tool, which is being positioned by a surgeon during surgery, relative to a patient reference array (also "dynamic reference base" ("DRB")) attached to a patient. The reference arrays allow the camera tracking system to determine a pose of the surgical tool relative to anatomical structure imaged by a medical image of the patient and relative to the patient. The surgeon can thereby use real-time visual feedback of the pose to navigate the surgical tool during a surgical procedure on the patient.

Surgical navigation of instruments using reference elements has become a well-established technique in the operating room. FIG. 10 illustrates an example of a trackable instrument 1010. The CAD model of an instrument 1010 is associated with a reference element 1020, so that the CAD model can be overlaid on registered images of patient's anatomy. To ensure fidelity of the overlay, accuracy of the instrument 1010 needs to be verified prior to use. The accuracy check is typically done via bringing the tip 1040 of the tracked instrument into a divot 1050 associated with another reference element. The divot 1050 is typically a cone-shaped depression ending in an apex.

The theoretical position of the tip 1040 is then compared with theoretical position of the divot 1050. Assuming the user has properly positioned the instrument 1010 in the divot 1050, the distance between the two positions determines the accuracy of tracked instrument 1010. If the accuracy check does not pass, that instrument 1010 may not be used.

In some examples, a source of inaccuracy during the accuracy check arises due to it being challenging for a user to place an instrument accurately in the divot. The ideal position for a sharp instrument is along normal from the apex to the base of the cone of the divot. Any deviation of the angle introduces small errors. Furthermore, a bad-acting user may move the position of the instrument to produce a false accuracy number (that appears more accurate).

In additional or alternative examples, a source of inaccuracy during the accuracy check arises due inaccuracy in tracking of the two reference elements (one associated with the tracked instrument and one associated with the divot). The reference element arrays are typically small in size (e.g., on a few centimeters wide) to minimize obstruction of the surgical area. The number of markers is also usually limited to optimize costs and workflow. A larger array with more markers can improve the accuracy of divot position.

In additional or alternative examples, a source of inaccuracy during the accuracy check arises due to a shape of the instrument tip. Blunt tip instruments may not fit well inside the divot and instruments with angled tips or a hook shape can make it even more difficult to properly place the instrument tip in the divot.

In additional or alternative examples, a sources of inaccuracies during the accuracy check includes a deformed instrument. In additional or alternative examples, the source of inaccuracies includes a deformed reference element. Note that a slight angular shift in the reference element can result in very small error for tracking of the reference element, but may result in a much larger error at instrument tip. In additional or alternative examples, the source of inaccuracies include inaccuracies in optical markers due to manufacturing defects, smudges, or inaccurate mounting of optical markers on mounting posts. All these are solvable problems, though. If an instrument can be calibrated at the time of use, the fidelity of tracking can be improved so that the physical tip matches the estimated tip.

SUMMARY

Some embodiments of the present disclosure are directed to performing an accuracy check and calibrating tracked instruments used in surgical procedures.

In some embodiments, a system configured to perform an accuracy check of a tracked instrument is provided. The system includes processing circuitry and memory coupled to the processing circuitry. The memory has instructions stored therein that are executable by the processing circuitry to cause the system to perform operations. The operations include determining a virtual position within a virtual space of a display device. The operations further include determining a virtual position within the virtual space of the tracked instrument. The operations further include determining a point of contact on the display device between the tracked instrument and the display device. The operations further include determining an expected point of contact on the display device between the tracked instrument and the display device based on the virtual position of the display device and the virtual position of the tracked instrument. The operations further include determining whether the tracked instrument is accurate based on a difference between the point of contact and the expected point of contact.

In other embodiments, a system configured to perform an accuracy check of a tracked instrument is provided. The system includes processing circuitry and memory coupled to the processing circuitry. The memory has instructions stored therein that are executable by the processing circuitry to cause the system to perform operations. The operations include determining a first virtual position within a virtual space of an emitter of an imaging device. The operations further include determining a first virtual position within the virtual space of a detector of the imaging device. The operations further include determining a first virtual position within the virtual space of the tracked instrument while the tracked instrument is at a first physical position between the emitter and the detector. The operations further include determining a first expected image of the tracked instrument based on the first virtual position of the emitter, the first virtual position of the detector, and the first virtual position of the tracked instrument. The operations further include obtaining a first image of the tracked instrument while it is positioned at the first physical position between the emitter and the detector. The operations further include determining a second virtual position within the virtual space of the emitter of the imaging device. The operations further include determining a second virtual position within the virtual space of the detector of the imaging device. The operations further include determining a second virtual position within the virtual space of the tracked instrument while the tracked instrument is at a second physical position between the emitter and the detector. The operations further include determining a second expected image of the tracked instrument based on the second virtual position of the emitter, the second virtual position of the detector, and the second virtual position of the tracked instrument. The operations further include obtaining a second image of the tracked instrument while it is positioned between the emitter and the detector, the second image being different than the first image. The operations further include determining whether the tracked instrument is accurate based on the first expected image, the second expected image, the first image, and the second image.

In other embodiments, a system configured to perform an accuracy check of a tracked instrument is provided. The system includes processing circuitry and memory coupled to the processing circuitry. The memory has instructions stored therein that are executable by the processing circuitry to cause the system to perform operations. The operations include determining a virtual position within a virtual space of the tracked instrument relative to a display device. The operations further include displaying an indication of the virtual position of the tracked instrument on the display device. The operations further include receiving an indication of an actual position of the tracked instrument relative to the display device. The operations further include determining whether the tracked instrument is accurate based on the indication of the actual position relative to the virtual position of the tracked instrument.

Other systems and corresponding methods and computer program products according to embodiments of the inventive subject matter will be or become apparent to one with skill in the art upon review of the following drawings and detailed description. It is intended that all such additional camera tracking system, methods. and computer program products be included within this description, be within the scope of the present inventive subject matter, and be protected by the accompanying claims. Moreover, it is intended that all embodiments disclosed herein can be implemented separately or combined in any way and/or combination.

DESCRIPTION OF THE DRAWINGS

Aspects of the present disclosure are illustrated by way of example and are not limited by the accompanying drawings. In the drawings:

FIG. 3 further illustrates the camera tracking system and the surgical robot configured according to some embodiments;

FIGS. 6A-C respectively illustrate a surgical robot with an end-effector, an expanded view of the end-effector, and a surgical tool in accordance with some embodiments;

FIG. 14 is a schematic diagram illustrating an example of a C-arm imaging device according to some embodiments;

FIGS. 15A-B are schematic diagrams illustrating images taken of a tracked instrument using the C-arm imaging device at two different positions according to some embodiments;

DETAILED DESCRIPTION

Figure 1:
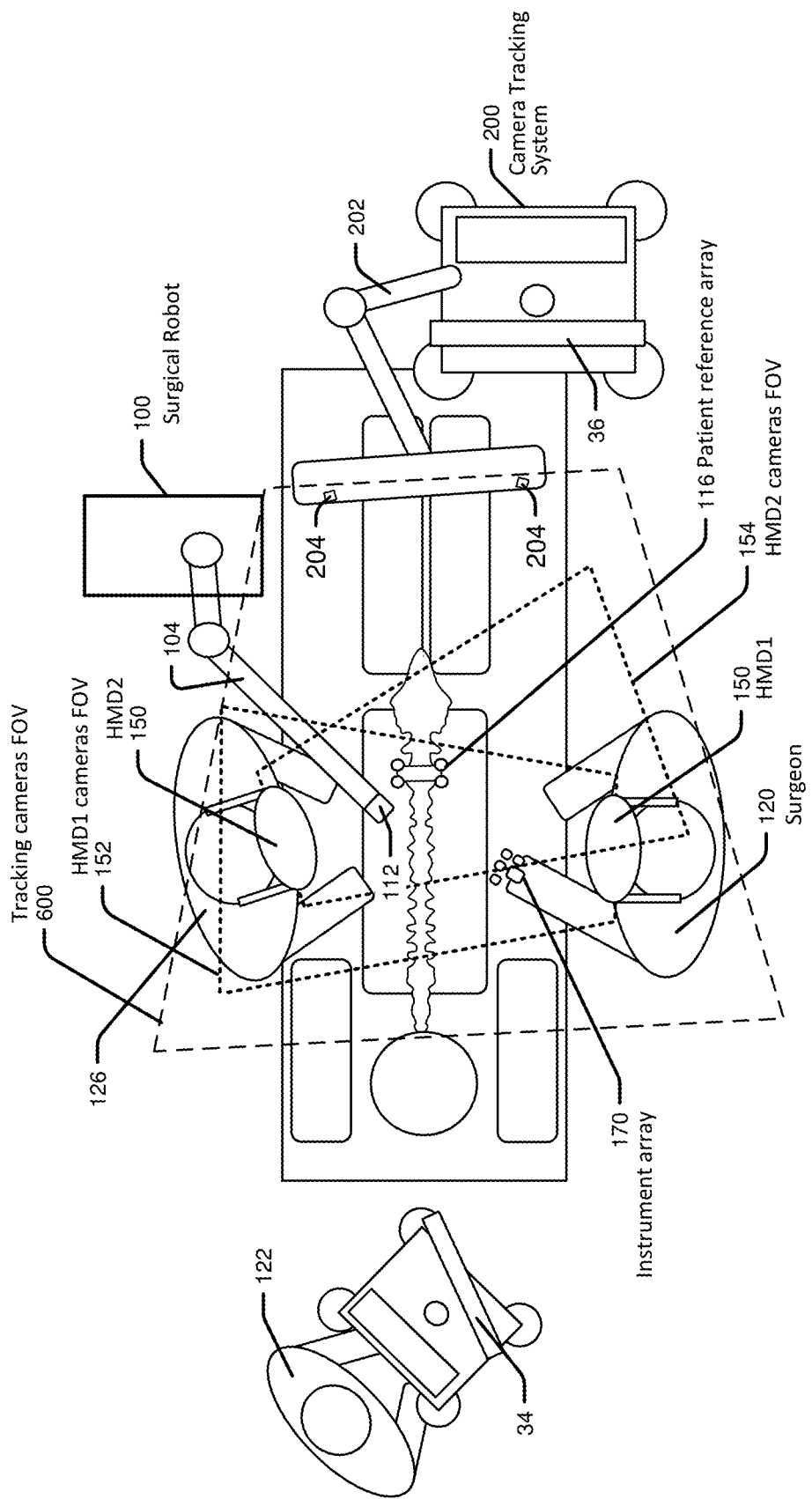
FIG. 1 is an overhead view of personnel wearing extended reality ("XR") headsets during a surgical procedure in a surgical room that includes a camera tracking system for navigated surgery and which may further include a surgical robot for robotic assistance according to some embodiments.

It is to be understood that the present disclosure is not limited in its application to the details of construction and the arrangement of components set forth in the description herein or illustrated in the drawings. The teachings of the present disclosure may be used and practiced in other embodiments and practiced or carried out in various ways. Also, it is to be understood that the phraseology and terminology used herein is for the purpose of description and should not be regarded as limiting. The use of "including," "comprising," or "having" and variations thereof herein is meant to encompass the items listed thereafter and equivalents thereof as well as additional items. Unless specified or limited otherwise, the terms "mounted," "connected," "supported," and "coupled" and variations thereof are used broadly and encompass both direct and indirect mountings, connections, supports, and couplings. Further, "connected" and "coupled" are not restricted to physical or mechanical connections or couplings.

The following discussion is presented to enable a person skilled in the art to make and use embodiments of the present disclosure. Various modifications to the illustrated embodiments will be readily apparent to those skilled in the art, and the principles herein can be applied to other embodiments and applications without departing from embodiments of the present disclosure. Thus, the embodiments are not intended to be limited to embodiments shown, but are to be accorded the widest scope consistent with the principles and features disclosed herein. The following detailed description is to be read with reference to the figures, in which like elements in different figures have like reference numerals. The figures, which are not necessarily to scale, depict selected embodiments and are not intended to limit the scope of the embodiments. Skilled artisans will recognize the examples provided herein have many useful alternatives and fall within the scope of the embodiments.

Various embodiments of the present disclosure are directed to providing operations by the camera tracking system to improve registration of candidate markers, such as a surveillance marker, when phantom markers appear in frames of tracking data from tracking cameras. Before describing these embodiments is detail, various components that may be used for performing embodiments in a navigated surgery system are described with reference to FIGS. 1-9.

Figure 2:
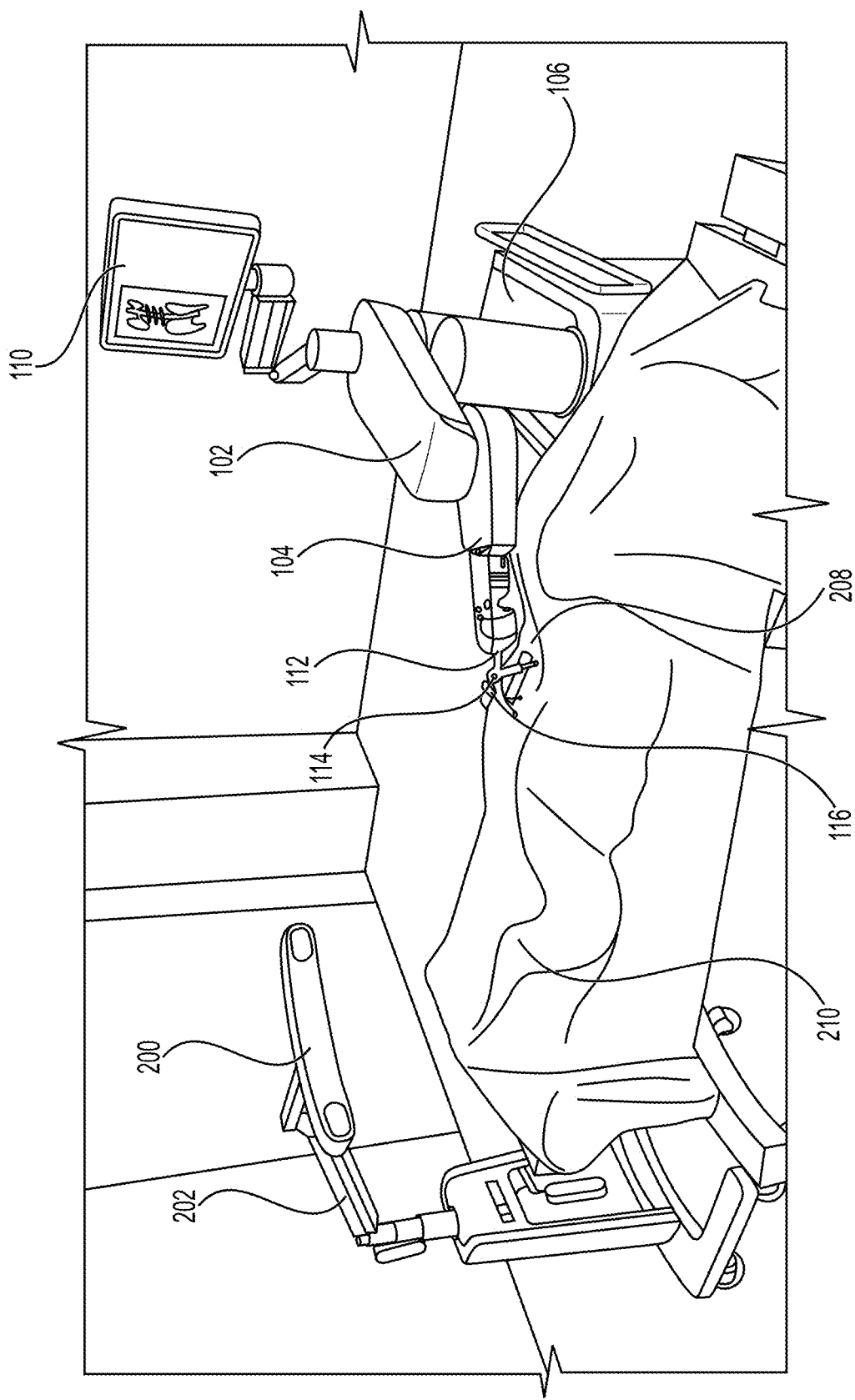
FIG. 2 illustrates the camera tracking system and the surgical robot positioned relative to a patient according to some embodiments.
Figure 4:
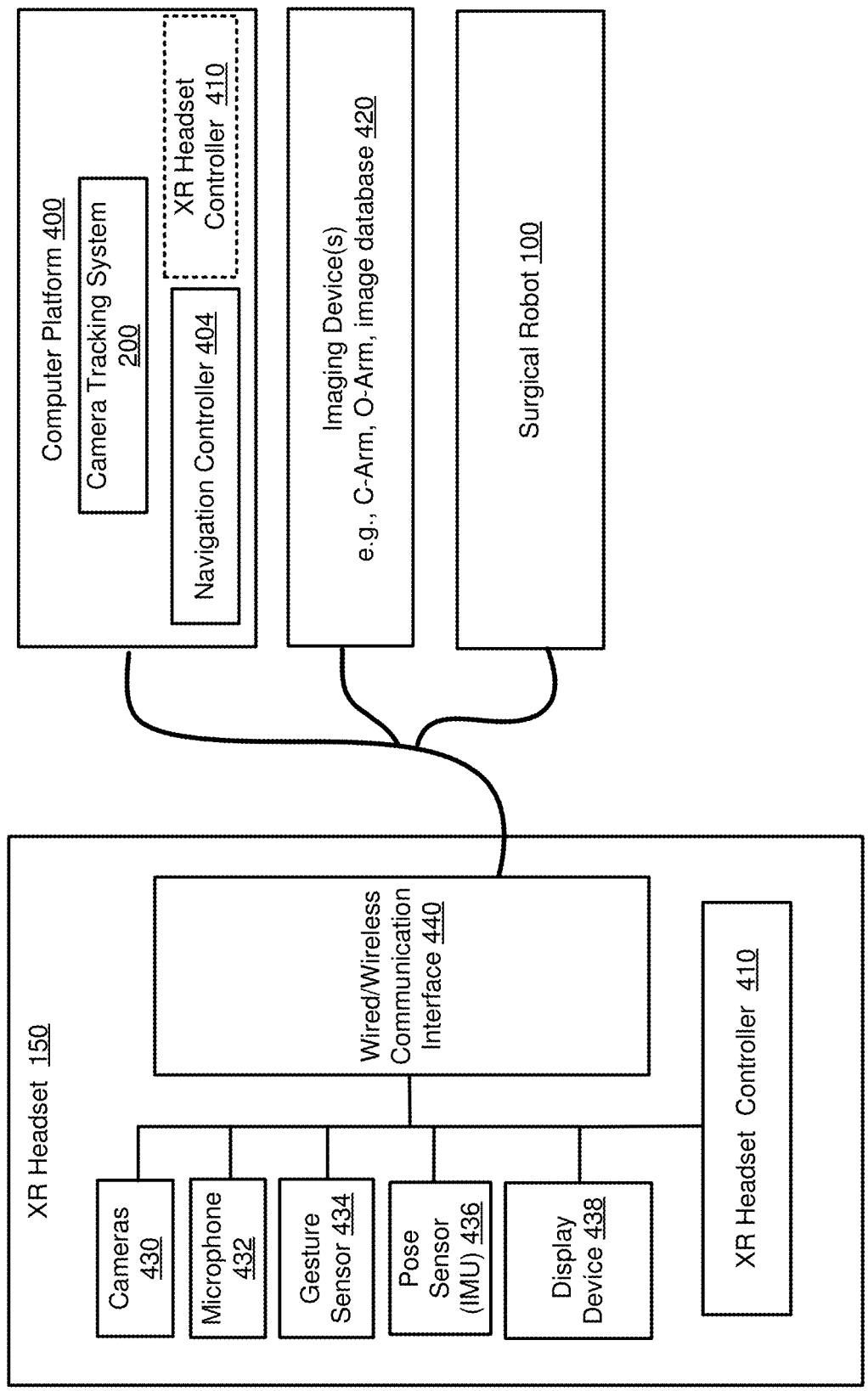
FIG. 4 illustrates a block diagram of a surgical system that includes an XR headset, a computer platform, imaging devices, and a surgical robot which are configured to operate according to some embodiments.
Figure 5:
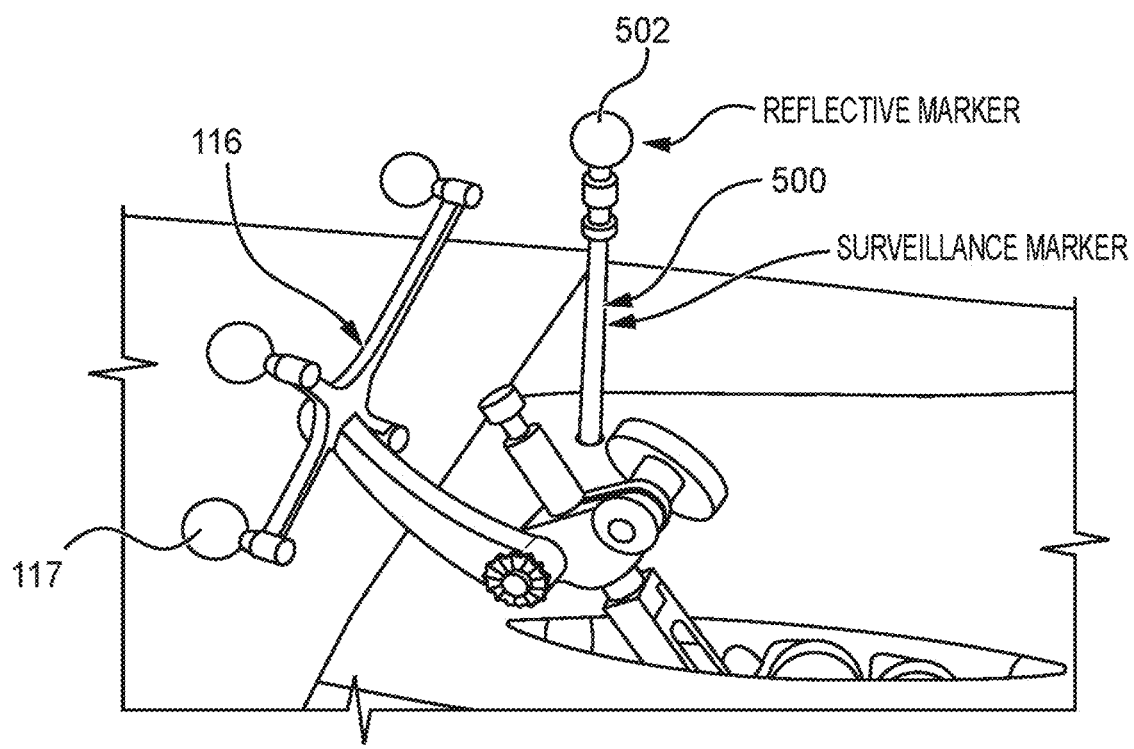
FIG. 5 illustrates a patient reference array ("DRB") and a surveillance marker.

FIG. 1 is an overhead view of personnel wearing extended reality ("XR") headsets 150 during a surgical procedure in a surgical room that includes a camera tracking system 200 for navigated surgery during a surgical procedure and which may further include a surgical robot 100 for robotic assistance, according to some embodiments. FIG. 2 illustrates the camera tracking system 200 and the surgical robot 100 positioned relative to a patient, according to some embodiments. FIG. 3 further illustrates the camera tracking system 200 and the surgical robot 100 configured according to some embodiments. FIG. 4 illustrates a block diagram of a surgical system that includes an XR headset 150, a computer platform 400, imaging devices 420, and the surgical robot 100 which are configured to operate according to some embodiments. FIG. 5 illustrates a patient reference array 116 (also "dynamic reference base" (DRB)) and a surveillance marker 500.

The XR headset 150 may be configured to augment a real-world scene with computer generated XR images. The XR headset 150 may be configured to provide an augmented reality ("AR") viewing environment by displaying the computer generated XR images on a see-through display screen that allows light from the real-world scene to pass therethrough for combined viewing by the user. Alternatively, the XR headset 150 may be configured to provide a virtual reality ("VR") viewing environment by preventing or substantially preventing light from the real-world scene from being directly viewed by the user while the user is viewing the computer-generated AR images on a display screen. The XR headset 150 can be configured to provide both AR and VR viewing environments. Thus, the term XR headset can referred to as an AR headset or a VR headset.

Referring to FIGS. 1-5, the surgical robot 100 may include, for example, one or more robot arms 104, a display 110, an end-effector 112, for example, including a guide tube 114, and an end effector reference array which can include one or more tracking markers. A patient reference array 116 ("DRB") has a plurality of tracking markers 117 and is secured directly to the patient 210 (e.g., to a bone of the patient 210). A spaced apart surveillance marker 500 (FIG. 5) has a single marker 502 connected to a shaft that is secured directly to the patient 210 at a spaced apart location from the patient reference array 116. Another reference array 170 is attached or formed on an instrument, surgical tool, surgical implant device, etc.

The camera tracking system 200 includes tracking cameras 204 which may be spaced apart stereo cameras configured with partially overlapping field-of-views. The camera tracking system 200 can have any suitable configuration of arm(s) 202 to move, orient, and support the tracking cameras 204 in a desired location, and may contain at least one processor operable to track location of an individual marker and pose of an array of markers. As used herein, the term "pose" refers to the location (e.g., along 3 orthogonal axes) and/or the rotation angle (e.g., about the 3 orthogonal axes) of markers (e.g., DRB) relative to another marker (e.g., surveillance marker) and/or to a defined coordinate system (e.g., camera coordinate system). A pose may therefore be defined based on only the multidimensional location of the markers relative to another marker and/or relative to the defined coordinate system, based on only the multidimensional rotational angles of the markers relative to the other marker and/or to the defined coordinate system, or based on a combination of the multidimensional location and the multidimensional rotational angles. The term "pose" therefore is used to refer to location, rotational angle, or combination thereof.

The tracking cameras 204 may include, e.g., infrared cameras (e.g., bifocal or stereophotogrammetric cameras), operable to identify, for example, active and passive tracking markers for single markers (e.g., surveillance marker 500) and reference arrays which can be formed on or attached to the patient 210 (e.g., patient reference array, DRB), end effector 112 (e.g., end effector reference array), XR headset (s) 150 worn by a surgeon 120 and/or a surgical assistant 126, etc. in a given measurement volume of a camera coordinate system while viewable from the perspective of the tracking cameras 204. The tracking cameras 204 may scan the given measurement volume and detect light that is emitted or reflected from the markers in order to identify and determine locations of individual markers and poses of the reference arrays in three-dimensions. For example, active reference arrays may include infrared-emitting markers that are activated by an electrical signal (e.g., infrared light emitting diodes ("LEDs")), and passive reference arrays may include retro-reflective markers that reflect infrared light (e.g., they reflect incoming IR radiation into the direction of the incoming light), for example, emitted by illuminators on the tracking cameras 204 or other suitable device.

The XR headsets 150 may each include tracking cameras (e.g., spaced apart stereo cameras) that can track location of a surveillance marker and poses of reference arrays within the XR camera headset field-of-views ("FOVs") 152 and 154, respectively. Accordingly, as illustrated in FIG. 1, the location of the surveillance marker and the poses of reference arrays on various objects can be tracked while in the FOVs 152 and 154 of the XR headsets 150 and/or a FOV 600 of the tracking cameras 204.

FIGS. 1-2 illustrate a potential configuration for the placement of the camera tracking system 200 and the surgical robot 100 in an operating room environment. Computer-aided navigated surgery can be provided by the camera tracking system controlling the XR headsets 150 and/or other displays 34, 36, and 110 to display surgical procedure navigation information. The surgical robot 100 is optional during computer-aided navigated surgery.

The camera tracking system 200 may operate using tracking information and other information provided by multiple XR headsets 150 such as inertial tracking information and optical tracking information (frames of tracking data). The XR headsets 150 operate to display visual information and may play-out audio information to the wearer.

This information can be from local sources (e.g., the surgical robot 100 and/or other medical), remote sources (e.g., patient medical image server), and/or other electronic equipment. The camera tracking system 200 may track markers in 6 degrees-of-freedom ("6DOF") relative to three axes of a 3D coordinate system and rotational angles about each axis. The XR headsets 150 may also operate to track hand poses and gestures to enable gesture-based interactions with "virtual" buttons and interfaces displayed through the XR headsets 150 and can also interpret hand or finger pointing or gesturing as various defined commands. Additionally, the XR headsets 150 may have a 1-10× magnification digital color camera sensor called a digital loupe. In some embodiments, one or more of the XR headsets 150 are minimalistic XR headsets that display local or remote information but include fewer sensors and are therefore more lightweight.

An "outside-in" machine vision navigation bar supports the tracking cameras 204 and may include a color camera. The machine vision navigation bar generally has a more stable view of the environment because it does not move as often or as quickly as the XR headsets 150 while positioned on wearers' heads. The patient reference array 116 (DRB) is generally rigidly attached to the patient with stable pitch and roll relative to gravity. This local rigid patient reference 116 can serve as a common reference for reference frames relative to other tracked arrays, such as a reference array on the end effector 112, instrument reference array 170, and reference arrays on the XR headsets 150.

During a surgical procedure using surgical navigation, the surveillance marker 500 is affixed to the patient to provide information on whether the patient reference array 116 has shifted. For example, during a spinal fusion procedure with planned placement of pedicle screw fixation, two small incisions are made over the posterior superior iliac spine bilaterally. The DRB and the surveillance marker are then affixed to the posterior superior iliac spine bilaterally. If the surveillance marker's 500 location changes relative to the patient reference array 116, the camera tracking system 200 may display a meter indicating the amount of movement and/or may display a pop-up warning message to inform the user that the patient reference array may have been bumped. If the patient reference array has indeed been bumped, the registration of the patient reference array to the tracked coordinate system may be invalid and could result in erroneous navigation which is off target.

When present, the surgical robot (also "robot") may be positioned near or next to patient 210. The robot 100 can be positioned at any suitable location near the patient 210 depending on the area of the patient 210 undergoing the surgical procedure. The camera tracking system 200 may be separated from the robot system 100 and positioned at the foot of patient 210. This location allows the tracking camera 200 to have a direct visual line of sight to the surgical area 208. In the configuration shown, the surgeon 120 may be positioned across from the robot 100, but is still able to manipulate the end-effector 112 and the display 110. A surgical assistant 126 may be positioned across from the surgeon 120 again with access to both the end-effector 112 and the display 110. If desired, the locations of the surgeon 120 and the assistant 126 may be reversed. An anesthesiologist 122, nurse or scrub tech can operate equipment which may be connected to display information from the camera tracking system 200 on a display 34.

With respect to the other components of the robot 100, the display 110 can be attached to the surgical robot 100 or in a remote location. End-effector 112 may be coupled to the robot arm 104 and controlled by at least one motor. In some embodiments, end-effector 112 can comprise a guide tube 114, which is configured to receive and orient a surgical instrument, tool, or implant used to perform a surgical procedure on the patient 210.

As used herein, the term "end-effector" is used interchangeably with the terms "end-effectuator" and "effectuator element." The term "instrument" is used in a non-limiting manner and can be used interchangeably with "tool" and "implant" to generally refer to any type of device that can be used during a surgical procedure in accordance with embodiments disclosed herein. Example instruments, tools, and implants include, without limitation, drills, screwdrivers, saws, dilators, retractors, probes, implant inserters, and implant devices such as a screws, spacers, interbody fusion devices, plates, rods, etc. Although generally shown with a guide tube 114, it will be appreciated that the end-effector 112 may be replaced with any suitable instrumentation suitable for use in surgery. In some embodiments, end-effector 112 can comprise any known structure for effecting the movement of the surgical instrument in a desired manner.

The surgical robot 100 is operable to control the translation and orientation of the end-effector 112. The robot 100 may move the end-effector 112 under computer control along x-, y-, and z-axes, for example. The end-effector 112 can be configured for selective rotation about one or more of the x-, y-, and z-axis, and a Z Frame axis, such that one or more of the Euler Angles (e.g., roll, pitch, and/or yaw) associated with end-effector 112 can be selectively computer controlled. In some embodiments, selective control of the translation and orientation of end-effector 112 can permit performance of medical procedures with significantly improved accuracy compared to conventional robots that utilize, for example, a 6DOF robot arm comprising only rotational axes. For example, the surgical robot 100 may be used to operate on patient 210, and robot arm 104 can be positioned above the body of patient 210, with end-effector 112 selectively angled relative to the z-axis toward the body of patient 210.

In some example embodiments, the XR headsets 150 can be controlled to dynamically display an updated graphical indication of the pose of the surgical instrument so that the user can be aware of the pose of the surgical instrument at all times during the procedure.

In some further embodiments, surgical robot 100 can be operable to correct the path of a surgical instrument guided by the robot arm 104 if the surgical instrument strays from the selected, preplanned trajectory. The surgical robot 100 can be operable to permit stoppage, modification, and/or manual control of the movement of end-effector 112 and/or the surgical instrument. Thus, in use, a surgeon or other user can use the surgical robot 100 as part of computer assisted navigated surgery, and has the option to stop, modify, or manually control the autonomous or semi-autonomous movement of the end-effector 112 and/or the surgical instrument.

Reference arrays of markers can be formed on or connected to robot arms 102 and/or 104, the end-effector 112 (e.g., end-effector array 114 in FIG. 2), and/or a surgical instrument (e.g., instrument array 170) to track poses in 6DOF along 3 orthogonal axes and rotation about the axes. The reference arrays enable each of the marked objects (e.g., the end-effector 112, the patient 210, and the surgical instruments) to be tracked by the tracking camera 200, and the tracked poses can be used to provide navigated guidance during a surgical procedure and/or used to control movement of the surgical robot 100 for guiding the end-effector 112 and/or an instrument manipulated by the end-effector 112.

Referring to FIG. 3 the surgical robot 100 may include a display 110, upper arm 102, lower arm 104, end-effector 112, vertical column 312, casters 314, a table 318, and ring 324 which uses lights to indicate statuses and other information. Cabinet 106 may house electrical components of surgical robot 100 including, but not limited, to a battery, a power distribution module, a platform interface board module, and a computer. The camera tracking system 200 may include a display 36, tracking cameras 204, arm(s) 202, a computer housed in cabinet 330, and other components.

In computer-assisted navigated surgeries, perpendicular 2D scan slices, such as axial, sagittal, and/or coronal views, of patient anatomical structure are displayed to enable user visualization of the patient's anatomy alongside the relative poses of surgical instruments. An XR headset or other display can be controlled to display one or more 2D scan slices of patient anatomy along with a 3D graphical model of anatomy. The 3D graphical model may be generated from a 3D scan of the patient, e.g., by a CT scan device, and/or may be generated based on a baseline model of anatomy which isn't necessarily formed from a scan of the patient.

Example Surgical System

FIG. 4 illustrates a block diagram of a surgical system that includes an XR headset 150, a computer platform 400, imaging devices 420, and a surgical robot 100 which are configured to operate according to some embodiments.

The imaging devices 420 may include a C-arm imaging device, an O-arm imaging device, and/or a patient image database. The XR headset 150 provides an improved human interface for performing navigated surgical procedures. The XR headset 150 can be configured to provide functionalities, e.g., via the computer platform 400, that include without limitation any one or more of: identification of hand gesture based commands, display XR graphical objects on a display device 438 of the XR headset 150 and/or another display device. The display device 438 may include a video projector, flat panel display, etc. The user may view the XR graphical objects as an overlay anchored to particular real-world objects viewed through a see-through display screen. The XR headset 150 may additionally or alternatively be configured to display on the display device 438 video streams from cameras mounted to one or more XR headsets 150 and other cameras.

Electrical components of the XR headset 150 can include a plurality of cameras 430, a microphone 432, a gesture sensor 434, a pose sensor (e.g., inertial measurement unit ("IMU")) 436, the display device 438, and a wireless/wired communication interface 440. The cameras 430 of the XR headset 150 may be visible light capturing cameras, near infrared capturing cameras, or a combination of both.

The cameras 430 may be configured to operate as the gesture sensor 434 by tracking for identification user hand gestures performed within the field of view of the camera(s) 430. Alternatively, the gesture sensor 434 may be a proximity sensor and/or a touch sensor that senses hand gestures performed proximately to the gesture sensor 434 and/or senses physical contact, e.g., tapping on the sensor 434 or its enclosure. The pose sensor 436, e.g., IMU, may include a multi-axis accelerometer, a tilt sensor, and/or another sensor that can sense rotation and/or acceleration of the XR headset 150 along one or more defined coordinate axes. Some or all of these electrical components may be contained in a head-worn component enclosure or may be contained in another enclosure configured to be worn elsewhere, such as on the hip or shoulder.

As explained above, a surgical system includes the camera tracking system 200 which may be connected to a computer platform 400 for operational processing and which may provide other operational functionality including a navigation controller 404 and/or of an XR headset controller 410. The surgical system may include the surgical robot 100. The navigation controller 404 can be configured to provide visual navigation guidance to an operator for moving and positioning a surgical tool relative to patient anatomical structure based on a surgical plan, e.g., from a surgical planning function, defining where a surgical procedure is to be performed using the surgical tool on the anatomical structure and based on a pose of the anatomical structure determined by the camera tracking system 200. The navigation controller 404 may be further configured to generate navigation information based on a target pose for a surgical tool, a pose of the anatomical structure, and a pose of the surgical tool and/or an end effector of the surgical robot 100, where the steering information is displayed through the display device 438 of the XR headset 150 and/or another display device to indicate where the surgical tool and/or the end effector of the surgical robot 100 should be moved to perform the surgical plan.

The electrical components of the XR headset 150 can be operatively connected to the electrical components of the computer platform 400 through the wired/wireless interface 440. The electrical components of the XR headset 150 may be operatively connected, e.g., through the computer platform 400 or directly connected, to various imaging devices 420, e.g., the C-arm imaging device, the I/O-arm imaging device, the patient image database, and/or to other medical equipment through the wired/wireless interface 440.

The surgical system may include a XR headset controller 410 that may at least partially reside in the XR headset 150, the computer platform 400, and/or in another system component connected via wired cables and/or wireless communication links. Various functionality is provided by software executed by the XR headset controller 410. The XR headset controller 410 is configured to receive information from the camera tracking system 200 and the navigation controller 404, and to generate an XR image based on the information for display on the display device 438.

The XR headset controller 410 can be configured to operationally process frames of tracking data from tracking cameras from the cameras 430 (tracking cameras), signals from the microphone 1620, and/or information from the pose sensor 436 and the gesture sensor 434, to generate information for display as XR images on the display device 438 and/or as other for display on other display devices for user viewing. Thus, the XR headset controller 410 illustrated as a circuit block within the XR headset 150 is to be understood as being operationally connected to other illustrated components of the XR headset 150 but not necessarily residing within a common housing or being otherwise transportable by the user. For example, the XR headset controller 410 may reside within the computer platform 400 which, in turn, may reside within the cabinet 330 of the camera tracking system 200, the cabinet 106 of the surgical robot 100, etc.

Turning now to FIGS. 6A-6C, the surgical robot system 100 relies on accurate positioning of the end-effector 112, surgical instruments 608, and/or the patient 210 (e.g., patient reference array 116) relative to the desired surgical area. In the embodiments shown in FIGS. FIGS. 6A-6C, the reference arrays include tracking markers 118, 804 which are rigidly attached to a portion of the instrument 608 and/or end-effector 112.

FIG. 6A depicts part of the surgical robot system 100 with the robot 102 including base 106, robot arm 104, and end-effector 112. The other elements, not illustrated, such as the display, marker tracking cameras, etc. may also be present as described herein. FIG. 6B depicts a close-up view of the end-effector 112 with guide tube 114 and a reference array that includes a plurality of tracking markers 118 rigidly affixed to the end-effector 112. In this embodiment, the plurality of tracking markers 118 are attached to the end-effector 112 configured as a guide tube. FIG. 6C depicts an instrument 608 (in this case, a probe) with a plurality of tracking markers 804 rigidly affixed to the instrument 608. As described elsewhere herein, the instrument 608 could include any suitable surgical instrument, such as, but not limited to, guide wire, cannula, a retractor, a drill, a reamer, a screwdriver, an insertion instrument, a removal instrument, or the like.

In FIG. 6C, the reference array 612 functions as the handle 620 of the instrument 608. Four markers 804 are attached to the handle 620 in a manner that is out of the way of the shaft 622 and tip 624. Stereophotogrammetric tracking by the tracking camera 200 of these four markers 804 allows the instrument 608 to be tracked as a rigid body and for the system 100 to precisely determine the location of the tip 624 and the orientation of the shaft 622 while the instrument 608 is moved within view of tracking camera 200.

To enable automatic tracking of one or more instruments 608, end-effector 112, or other object to be tracked in 3D (e.g., multiple rigid bodies), the markers 118, 804 on each instrument 608, end-effector 112, or the like, may be arranged asymmetrically with a known inter-marker spacing. The reason for asymmetric alignment is so that it is unambiguous which marker 118, 804 corresponds to a particular pose on the rigid body and whether markers 118, 804 are being viewed from the front or back, i.e., mirrored. For example, if the markers 118, 804 were arranged in a square on the instrument 608 or end-effector 112, it would be unclear to the system 100, 300, 600 which marker 118, 804 corresponded to which corner of the square. For example, for the instrument 608, it would be unclear which marker 804 was closest to the shaft 622. Thus, it would be unknown which way the shaft 622 was extending from the array 612. Accordingly, each array 612 and thus each instrument 608, end-effector 112, or other object to be tracked should have a unique marker pattern to allow it to be distinguished from other instruments 608 or other objects being tracked.

Asymmetry and unique marker patterns allow the tracking camera 200 and system 100 to detect individual markers 118, 804 then to check the marker spacing against a stored template to determine which instrument 608, end-effector 112, or another object they represent. Detected markers 118, 804 can then be sorted automatically and assigned to each tracked object in the correct order. Without this information, rigid body calculations could not then be performed to extract key geometric information, for example, such as instrument tip 624 and alignment of the shaft 622, unless the user manually specified which detected marker 118, 804 corresponded to which position on each rigid body.

Figure 7A:
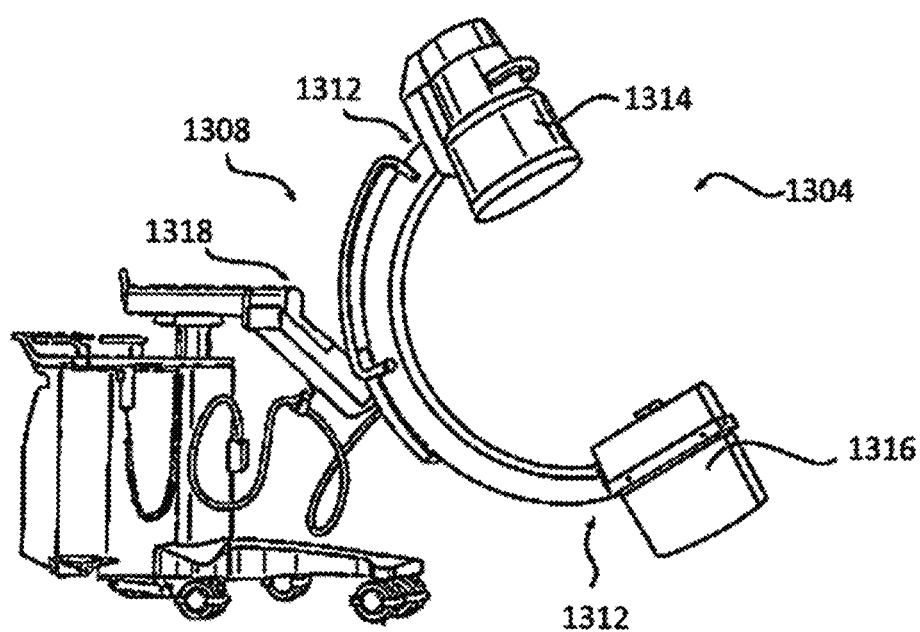
FIGS. 7A-B are schematic diagrams illustrating examples of imaging devices according to some embodiments.
Figure 7B:
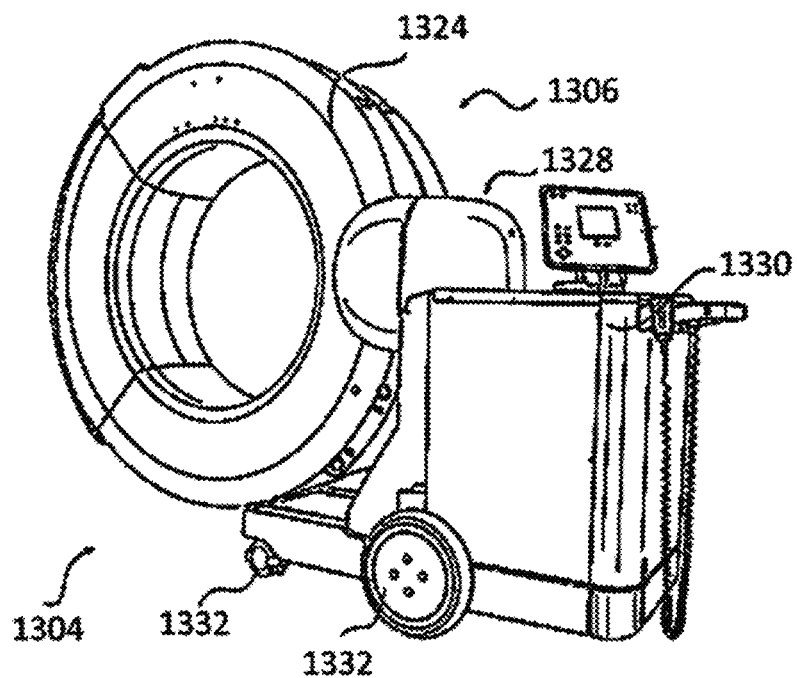

FIGS. 7A-B illustrate medical imaging systems 1304 that may be used in conjunction with robot system 100 and/or navigation systems to acquire pre-operative, intra-operative, post-operative, and/or real-time image data of patient 210. Any appropriate subject matter may be imaged for any appropriate procedure using the imaging system 1304. The imaging system 1304 may be any imaging device such as a C-arm 1308 device, an O-arm 1306 device, a fluoroscopy imaging device, a magnetic resonance imaging scanner, etc. It may be desirable to take x-rays of patient 210 from a number of different positions, without the need for frequent manual repositioning of patient 210 which may be required in an x-ray system. As illustrated in FIG. 7A, the imaging system 1304 may be in the form of a C-arm 1308 that includes an elongated C-shaped member terminating in opposing distal ends 1312 of the "C" shape. C-shaped member 1130 may further comprise an x-ray source 1314 and an image receptor 1316. The space within C-arm 1308 of the arm may provide room for the physician to attend to the patient substantially free of interference from x-ray support structure 1318. As illustrated in FIG. 7B, the imaging system 1304 may include an O-arm imaging device 1306 having a gantry housing 1324 attached to a support structure imaging device support structure 1328, such as a wheeled mobile cart 1330 with wheels 1332, which may enclose an image capturing portion, not illustrated. The image capturing portion may include an x-ray source and/or emission portion and an x-ray receiving and/or image receiving portion, which may be disposed about one hundred and eighty degrees from each other and mounted on a rotor (not illustrated) relative to a track of the image capturing portion. The image capturing portion may be operable to rotate three hundred and sixty degrees during image acquisition. The image capturing portion may rotate around a central point and/or axis, allowing image data of patient 210 to be acquired from multiple directions or in multiple planes. Although certain imaging systems 1304 are exemplified herein, it will be appreciated that any suitable imaging system may be selected by one of ordinary skill in the art.

Figure 8:
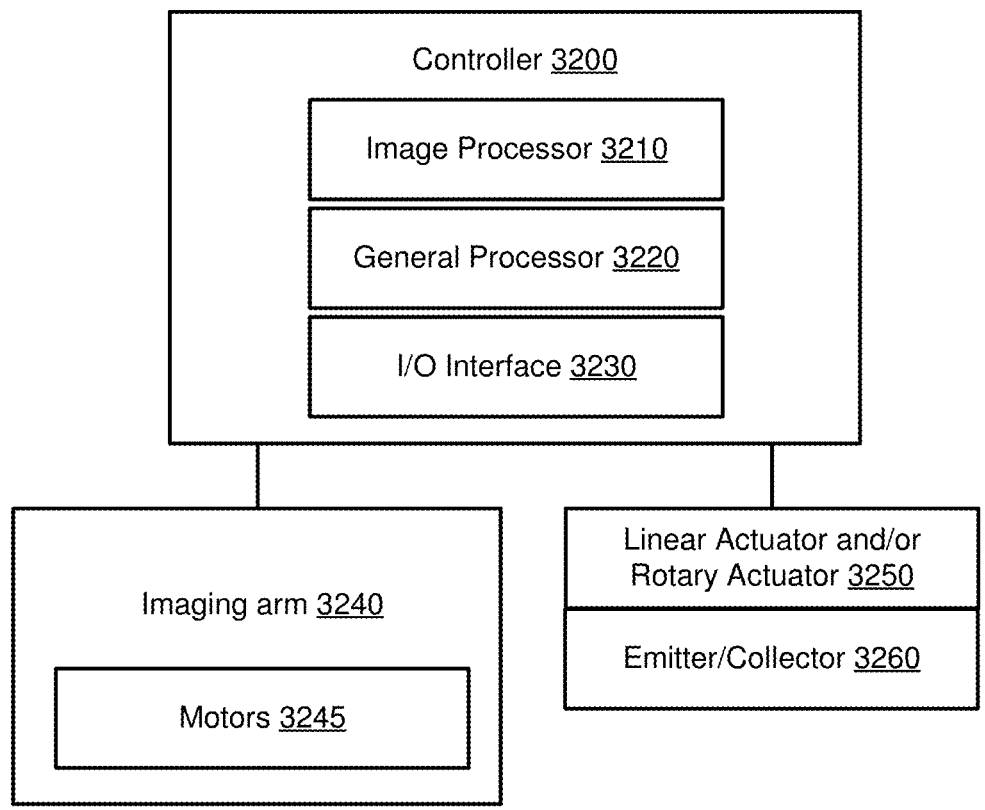
FIG. 8 is a block diagram illustrating an example of an imaging system according to some embodiments.

FIG. 8 illustrates a block diagram of components of a medical imaging system configured in accordance with some embodiments of the present disclosure. The medical imaging system includes a controller 3200, a imaging arm 3240 (e.g., a C-arm or an O-arm), a linear actuator and/or rotary actuator 3250 connected to an X-ray beam emitter or collector 3260. The controller 3200 includes an image processor 3210, a general processor 3220, and an I/O interface 3230. The image processor 3210 performs image processing to combine sets of images to generate a three-dimensional image of the scanned volume. The general processor 3220 is used to perform various embodiments of the present disclosure. The I/O interface 3230 communicatively couples the controller 3200 to other components of the medical imaging system. The imaging arm 3240 includes motors 3245 used to move the collector and emitter along an arc, e.g., three hundred and sixty degrees, during image acquisition. Motors 3245 are controlled by C-arm the controller 3200. The controller 3200 can also control movement of the linear actuator and/or rotary actuator 3250.

Figure 9:
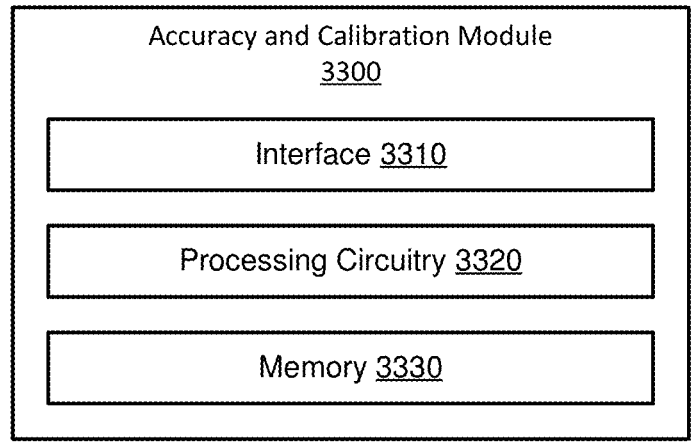
FIG. 9 is a block diagram illustrating an example of an accuracy and calibration module according to some embodiments.
Figure 10:
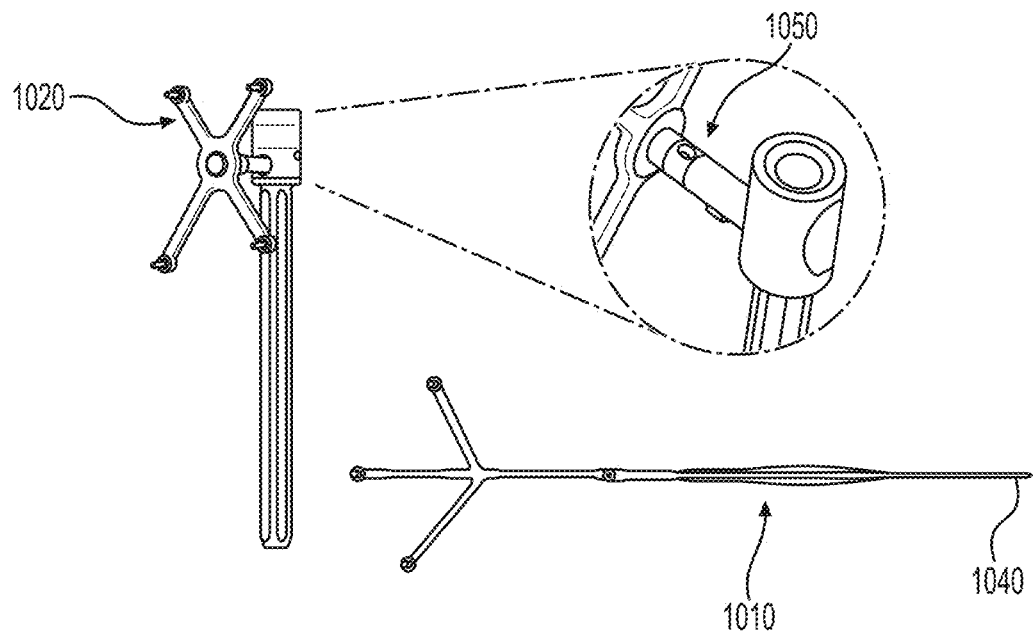
FIG. 10 is a schematic diagram illustrating an example of a tracked instrument according to some embodiments.

FIG. 9 illustrates an example of an accuracy and calibration module 3300. The accuracy and calibration module 3330 can include an interface 3310, a processing circuitry 3320, and a memory 3330. In some examples, the accuracy and calibration module is part of a system (e.g., an imaging system or a camera tracking system). The memory 3330 can include instructions stored therein that are executable by the processing circuitry to perform operations according to some embodiments herein.

Embodiments that include performing an accuracy check and/or calibrating of a tracked instrument based on contact with a touch sensor (e.g., a touchscreen of a display device) are described below.

In some embodiments, multiple points of contact (e.g., touch positions from the tip of a tracked instrument) can be detected by one or more touchpads that are themselves tracked by navigation camera. The instruments and the pressure touchpads can each have associated reference elements that are tracked by the navigation camera. In some examples, the touchpads are sensitive to pressure, capacitance, or resistance.

Figure 11:
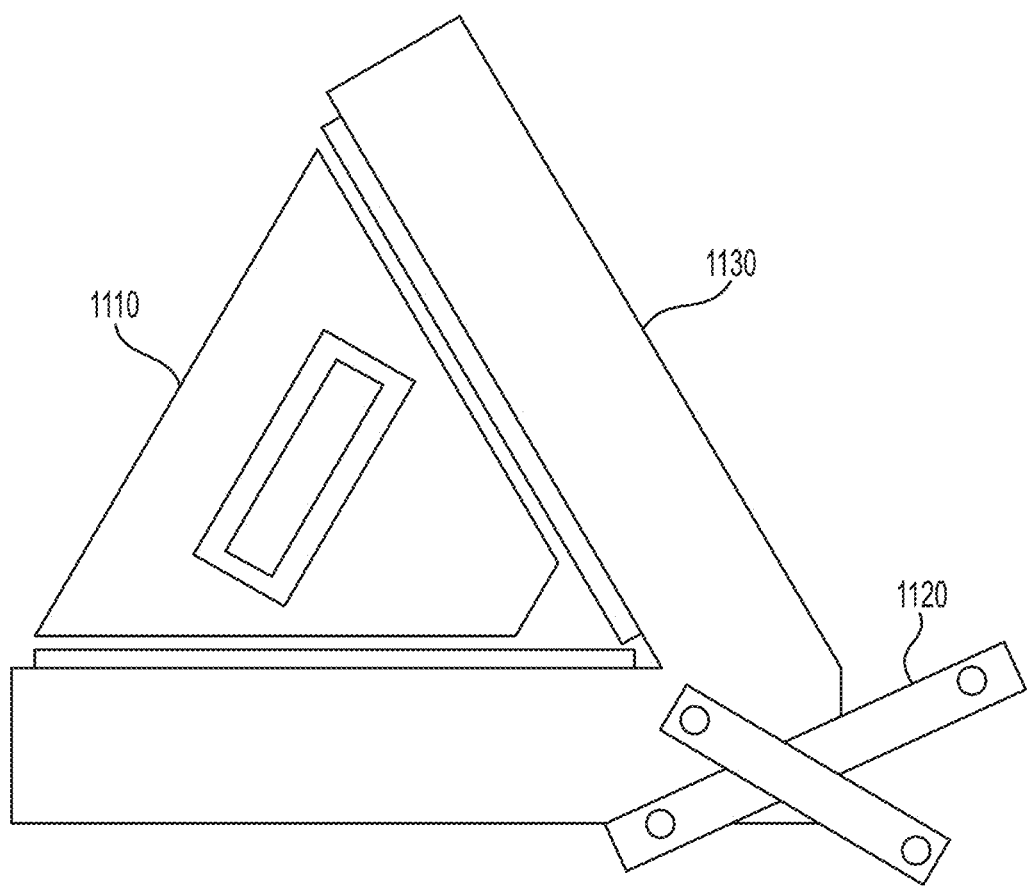
FIG. 11 is a schematic diagram illustrating an example of a set of display devices configured to interact with a tracked instrument according to some embodiments.

FIG. 11 illustrates an example of a set of touchpads 1110 coupled together to create an opening for accepting a tip of the tracked instrument. The associated reference element 1120 is coupled to the touchpads. In this example, the touchpads and reference arrays are securely housed in a supporting structure 1130 to reduce movement.

The touchpads 1110 can capture location of pressure points. Resistive touchpads are especially useful, since they do not rely on capacitance of the object. When an instrument is brought in the wedge, it touches at least two points on the touchpads 1110. The touchpads 1110 then send the location of sensed points to the system. The system also receives the position of pose of the touchpads and instruments via their associated reference elements 1120. Thus, the system can calculate the theoretical position of the tip of the instrument under test. It can then compare the tip location to the location reported by the three touchpads 1110.

Typically, the bottom touchpad would report position of a sharp or semi-sharp instrument tip. For a broader instrument, such as an Osteotome, there will be multiple touch-points on the bottom touchpads while the side touchpads will report straight lines of touch-points. The approximate position of the CAD model with respect to the touchpads is known already to the system based on the tracking information reported by the camera. Thus, the accuracy of the physical model can be calculated.

Figure 12:
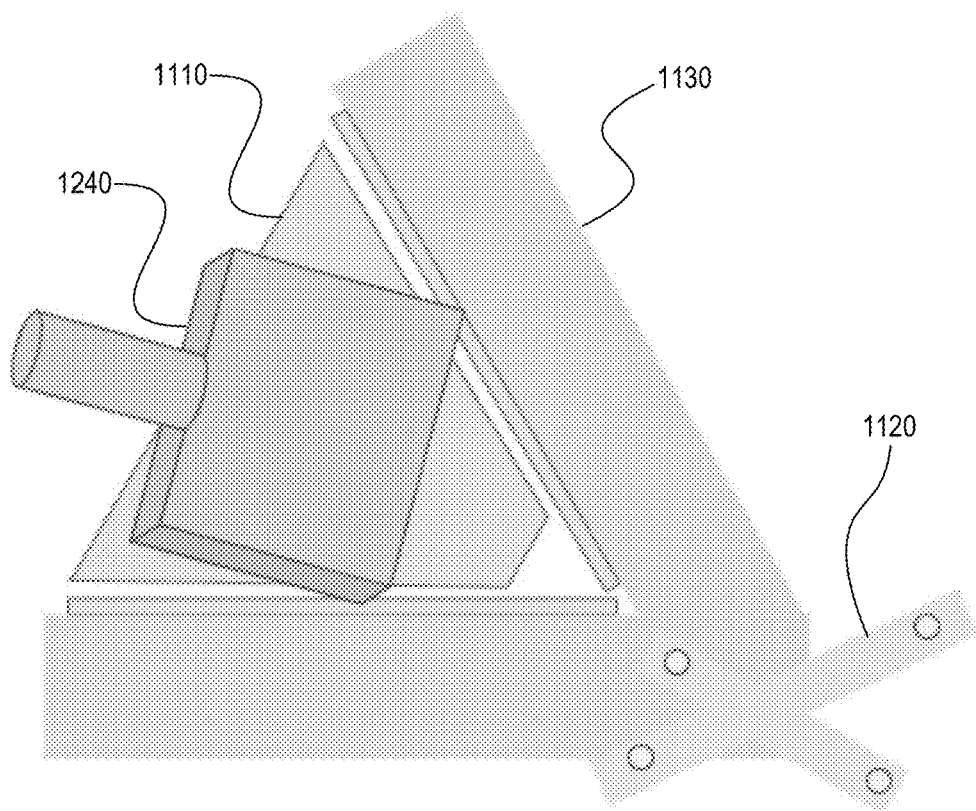
FIG. 12 is a schematic diagram illustrating an example of the set of display devices of FIG. 11 being contacted by a tracked instrument according to some embodiments.

FIG. 12 illustrates an example of a tip of a tracked instrument 1240 contacting the touchpads 1110. The wedge shape of the opening between the touchpads 1110 allows an accuracy check of instruments with tips that are too big to fit in a typical divot used in navigation arrays.

Figure 13:
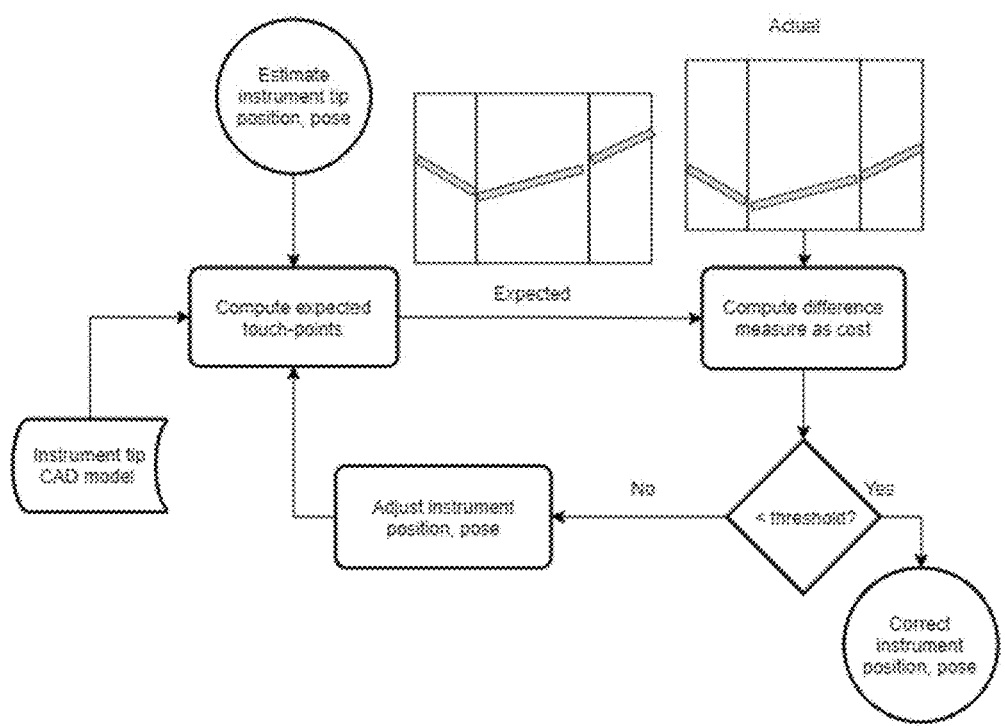
FIG. 13 is a flow chart illustrating an example of operations for performing an accuracy check on a tracked instrument based on contact with a display device according to some embodiments.

FIG. 13 illustrates an example of operations to perform an accuracy check and calibrate a tracked instrument based on contact between the tracked instrument and the display devices. To calibrate an instrument, the reported touchpad points are compared against the theoretical model. First, the user touches instrument tip on all three touchpads in a way that reference elements of both the instrument and the touchpad structure are visible to the tracking camera. The theoretical position of the instrument tip with respect to touchpads is then calculated. This serves as the initial position estimate of the instrument tip. Since the relative position of three touchpads is known, the theoretical touch-points of the CAD model for each touchpad are then calculated. The optimization tweaks the position and pose of the CAD model of the instrument to obtain a close match between the theoretical touchpoints and the actual ones as shown in the algorithm below.

In some embodiments, these operations improve accuracy checks for instruments without a sharp tip or instruments that are too wide to fit in a traditional divot. In additional or alternative embodiments, these operation allow re-calibration or correction of theoretical instrument tip location based on actual measurements.

Figure 18:
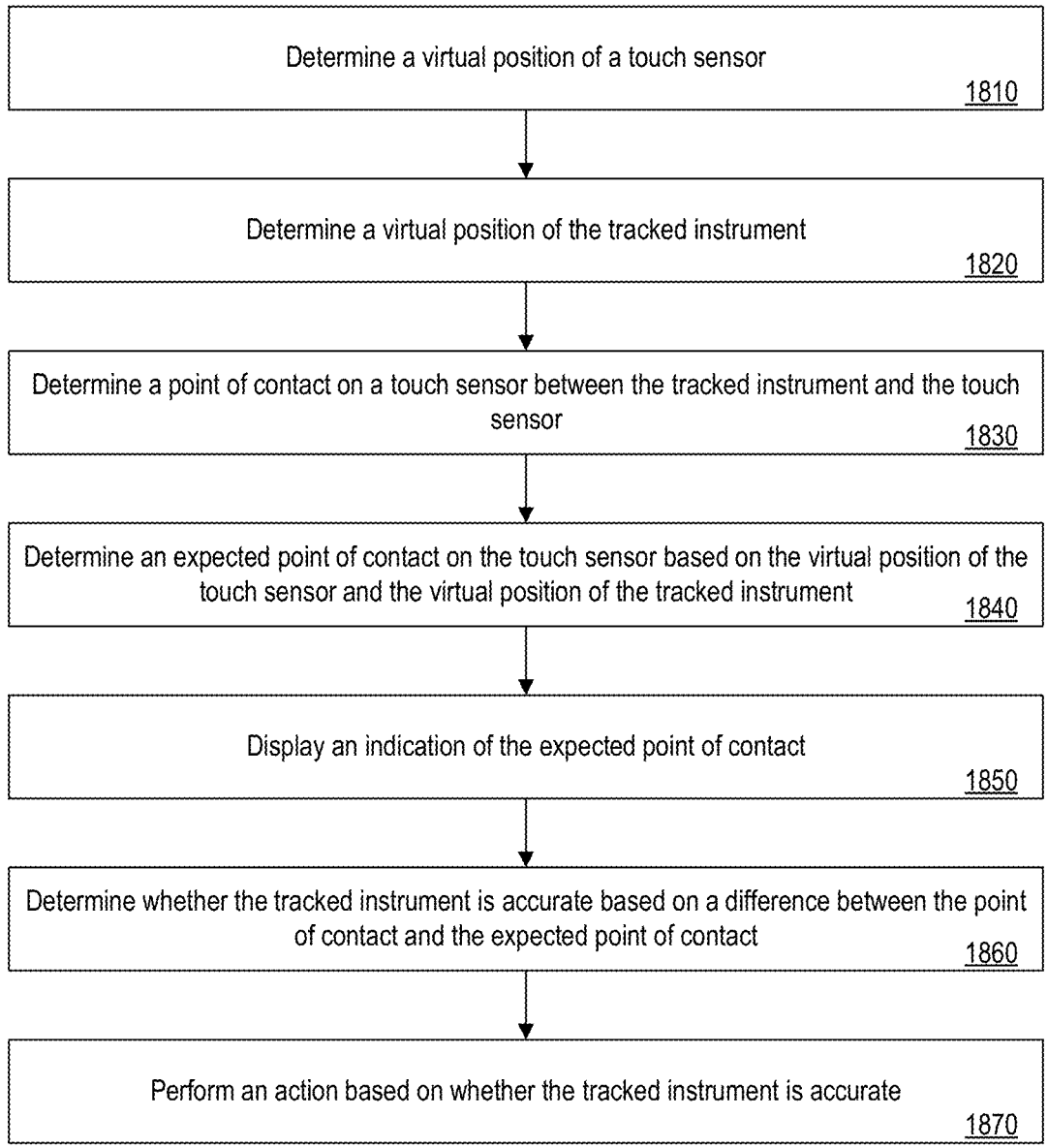
FIGS. 18-20 are flowcharts of operations performed by a system to perform an accuracy check of tracked instruments according to some embodiments.

FIG. 18 illustrates an example of operations performed by a system to perform an accuracy check and/or calibration of a tracked instrument based on a point of contact between the tracked instrument and a touch sensor. Although the operations are described below as being performed by the accuracy and calibration module 3300, any suitable system (e.g., an imaging system or a tracking system) can perform these operations.

At block 1810, processing circuitry 3320 determines a virtual position of the touch sensor. In some examples, the term virtual position is used herein to describe a virtual location and a virtual pose of an object. In some embodiments, the system includes a camera. Determining the virtual position of the touch sensor includes: determining information about a shape of the touch sensor relative to a reference element coupled to the touch sensor; capturing, via the camera, an image of the reference element coupled to the touch sensor; determining a virtual position of the reference element coupled to the touch sensor relative to a dynamic reference base ("DRB") based on the image of the reference element coupled to the touch sensor; and determining the virtual position of the touch sensor based on the information about the shape of the touch sensor and the virtual position of the reference element coupled to the touch sensor.

At block 1820, processing circuitry 3320 determines a virtual position of the tracked instrument. In some embodiments, the virtual position of the touch sensor and the virtual position of the tracked instrument are within the same virtual space (e.g., relative to a common reference point).

In additional or alternative embodiments, the system includes a camera. determining the virtual position of the tracked instrument includes: determining information about a shape of the tracked instrument relative to a reference element coupled to the tracked instrument; capturing, via the camera, an image of the reference element coupled to the tracked instrument; determining a virtual position of the reference element coupled to the tracked instrument relative to the DRB based on the image of the reference element coupled to the tracked instrument; and determining the virtual position of the tracked instrument based on the shape of the tracked instrument and the reference element coupled to the tracked instrument.

At block 1830, processing circuitry 3320 determines a point of contact on a touch sensor between the tacked instrument and the touch sensor. In some embodiments, the system includes the touch sensor and the touch sensor includes a touchscreen (e.g., a pressure sensitive, resistance sensitive, or capacitance sensitive touchscreen). In some examples the touch sensor is part of a display device. Determining the point of contact includes detecting a location on the touchscreen that the tracked instrument is touching.

In additional or alternative embodiments, the touch sensor includes a plurality of touch sensors coupled together to form an opening. Determining the point of contact on the touch sensor includes determining a plurality of points of contact, each point of contact between one of the touch sensors of the plurality of touch sensors and the tracked instrument while the tracked instrument is positioned in the opening.

At block 1840, processing circuitry 3320 determines an expected point of contact on the touch sensor based on the virtual position of the touch sensor and the virtual position of the tracked instrument.

In some embodiments, information about the shape of the tracked instrument is determined and the information an intended position of a tip of the tracked instrument relative to a reference element coupled to the tracked instrument. Determining the point of contact on the touch sensor can include determining a point of contact between the tip of the tracked instrument and the touch sensor. Determining the expected point of contact on the touch sensor can include determining a point of contact between the tip of the tracked instrument and the touch sensor based on the virtual position of the touch sensor and the virtual position of the tracked instrument.

At block 1850, processing circuitry 3320 displays an indication of the expected point of contact. In some embodiments, the system includes a display device that includes the touch sensor. Determining the point of contact on the touch sensor between the tracked instrument and the touch sensor includes receiving an indication of the point of contact on the touch sensor from a user in response to displaying the indication of the expected point of contact.

At block 1860, processing circuitry 3320 determines whether the tracked instrument is accurate based on a difference between the point of contact and the expected point of contact.

In some embodiments, determining the point of contact on the touch sensor includes determining a plurality of points of contact between the tracked instrument and the touch sensor. Determining the expected point of contact on the touch sensor includes determining a plurality of expected points of contact between the tracked instrument and the touch sensor based on the virtual position of the touch sensor and the virtual position of the tracked instrument. Determining whether the tracked instrument is accurate includes determining whether the tracked instrument is accurate based on a difference between the plurality of points of contact and the plurality of expected points of contact.

At block 1870, processing circuitry 3320 performs an action based on whether the tracked instrument is accurate.

In some embodiments, determining whether the tracked instrument is accurate includes determining that the difference exceeds a predetermined threshold. In some examples, performing the action includes outputting an indication that the tracked instrument is not suitable for use. In additional or alternative examples, performing the action includes calibrating a tracking system used to track the tracked instrument using at least one of the point of contact, the expected point of contact, and the difference.

Various operations of FIG. 18 may be optional. For example, blocks 1850 and 1870 may be optional in some embodiments.

Embodiments that include performing an accuracy check and/or calibrating a tracked instrument based on an image taken by a tracked imaging device are described below.

In some embodiments, multiple x-ray views of one or more tracked instruments are taken with a Fluoroscope that is tracked by a navigation camera using an attached registration fixture. Such registration fixtures are commonly used for surgical navigation using fluoroscopy.

FIG. 14 illustrates an example of an imaging device 1410 including an x-ray emitter 1420 and a x-ray detector 1430. The registration fixture 1440 is coupled to a predetermine portion of the imaging device 1410.

The registration fixture 1440 typically includes fiducials in two planes at known positions. These fiducials are then detected in images captured by a navigation camera. Using the known positions, the relative position of the emitter 1420 is then computed. The position of the detector 1440 is tracked using the attached reference element 1440 via a navigation camera. When an instrument tracked with a reference element is brought between the emitter and detector, its relative position with respect to registration fixture 1440 is calculated.

The CAD model of the associated instrument tip can then be projected on the fluoroscopy image to achieve navigation. Since the registration fixture can move after the x-ray image is captured, often a different reference element, called a DRB is solidly attached to the patient, so that all tracked positions are relative to the fixed DRB.

Since the rendered position of an instrument is only in 2D, at least two views, roughly orthogonal to each other, are used to track the instrument on two roughly orthogonal views to obtain pseudo-3D navigation.

FIGS. 15A-B illustrate an example in which a wedge-shaped tracked instrument is placed between the emitter 1420 and detector 1430, such that its views are captured by the fluoroscope in two positions. The corresponding images 1570*a-b* below the fluoroscope show the instrument profile in different angles. Note that most instruments are solid and are made up of metal, which absorbs most x-rays and shows up dark on an x-ray image.

Since the theoretical position of the tip of the instrument 1550 is known via the attached reference element 1560, the accuracy of the projection can be compared to the theoretical projection by detecting the dark instrument shape in a bright image. Thus, the accuracy can be calculated without needing a divot.

If multiple instruments can be placed within the field of view of the x-ray image, accuracy of all of them can be calculated simultaneously.

Figure 16:
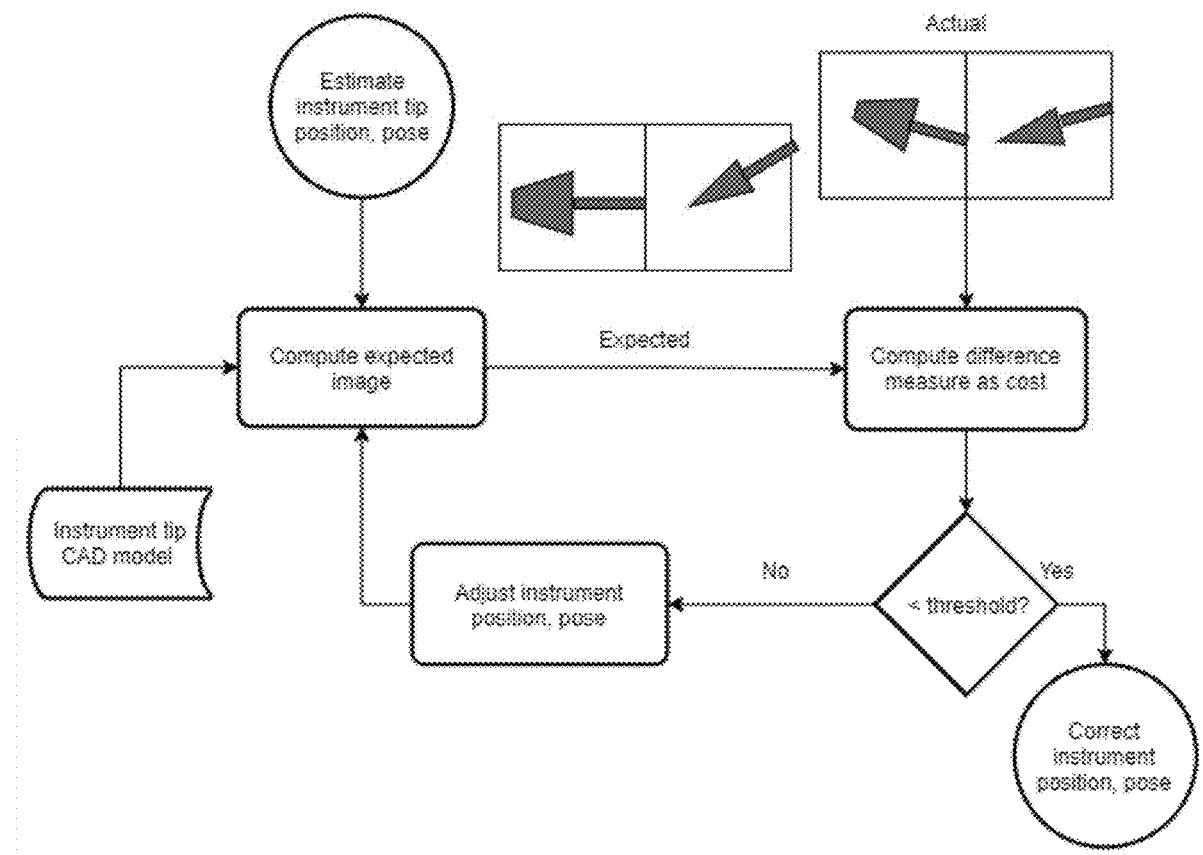
FIG. 16 is a flow chart illustrating an example of operations for performing an accuracy check on a tracked instrument based on images taken of the tracked instrument according to some embodiments.

FIG. 16 illustrates an example of operations for performing an accuracy check and/or calibrating a tracked instrument using images of the tracked instrument. The x-ray views of an instrument are obtained as described above. The theoretical position of the instrument tip projected in the views then calculated. This serves as the initial position estimate of the instrument tip. Using the projection matrix, the theoretical view of the CAD model in each x-ray is then calculated. The optimization tweaks the position and pose of the CAD model of the instrument to obtain a close match between the CAD view and actual image as shown in the algorithm below.

In some examples, this is the same problem as matching a CT scan to multiple Fluoroscopy images in CTFluoro registration, except in this case a CAD model is used instead of a CT scan to compute dynamically rendered radiograph ("DRR").

In some embodiments, these operations do not rely on a sharp tipped instrument fitting snugly in a divot, and can be used for accuracy checks of all types of instrument tips.

In additional or alternative embodiments, these operations improve accuracy checks for instruments without a sharp or straight tip.

In additional or alternative embodiments, these operations allow re-calibration or correction of theoretical instrument tip location based on actual measurements.

In additional or alternative embodiments, these operations enable accuracy checks and re-calibration of multiple instruments simultaneously.

Figure 19:
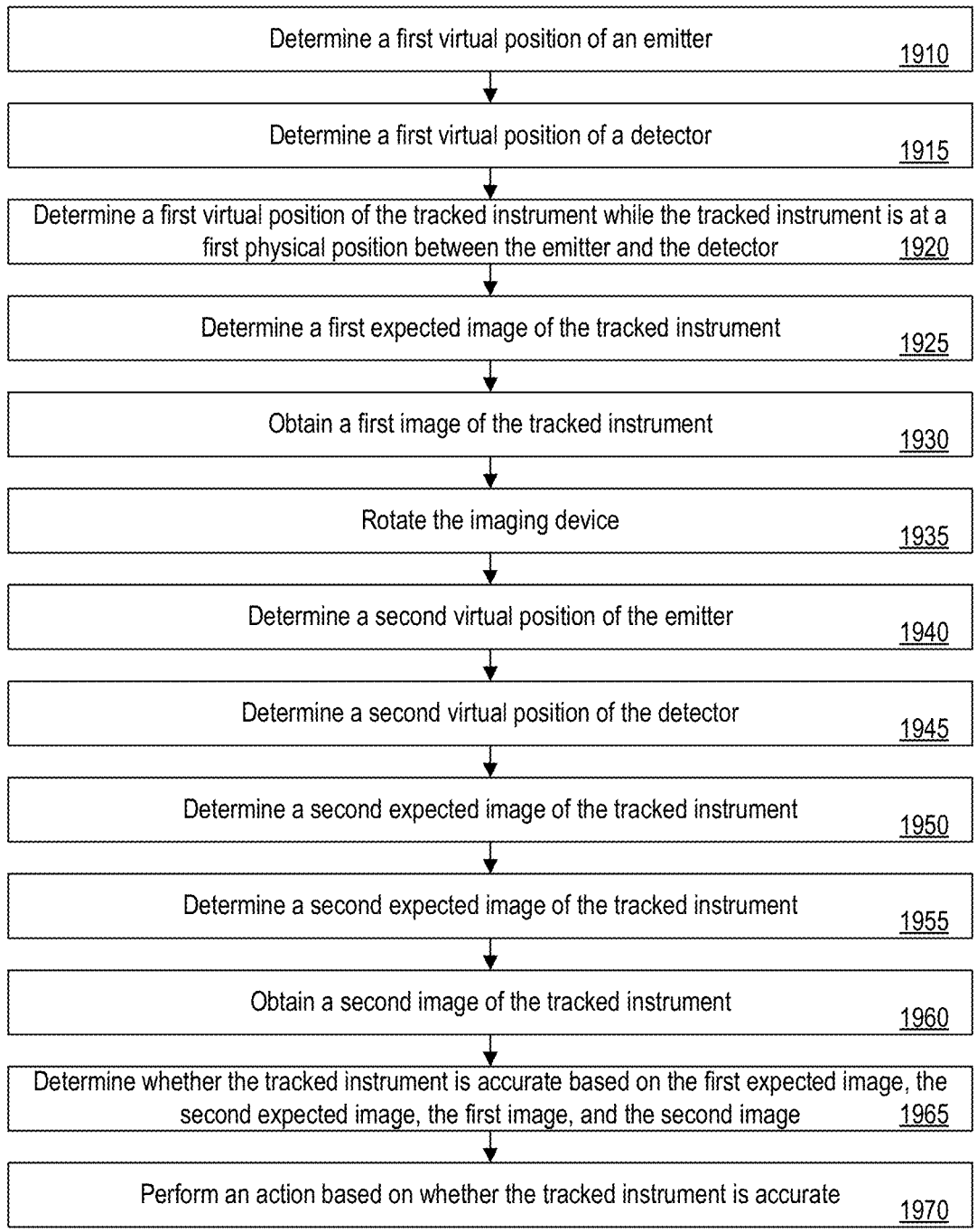

FIG. 19 illustrates an example of operations performed by a system to perform an accuracy check and/or calibration of a tracked instrument based on a pair of images taken by an imaging device. Although the operations are described below as being performed by the accuracy and calibration module 3300, any suitable system (e.g., an imaging system or a tracking system) can perform these operations.

At block 1910, processing circuitry 3320 determines a first virtual position of an emitter. In some embodiments, the system includes a tracking camera and an imaging device including the emitter and a detector. Determining the first virtual position of the emitter includes: capturing, via the camera, an image of a reference element coupled to the imaging device; determining a virtual position of the reference element coupled to the imaging device (e.g., relative to a dynamic reference base ("DRB")) based on the image of the reference element coupled to the imaging device; and determining the virtual position of the emitter based on predetermined information indicating a position of the emitter relative to the reference element coupled to the imaging device and the virtual position of the reference element coupled to the imaging device. In additional or alternative embodiments, the virtual position of the emitter is determined based on predetermined information indicating a position of the emitter relative to the detector and a virtual position of the detector.

At block 1915, processing circuitry 3320 determines a first virtual position of a detector. In some embodiments, the system includes a tracking camera and an imaging device including the emitter and the detector. Determining the first virtual position of the detector includes: capturing, via the camera, an image of a reference element coupled to the imaging device; determining a virtual position of the reference element coupled to the imaging device (e.g., relative to a DRB) based on the image of the reference element coupled to the imaging device; and determining the virtual position of the detector based on predetermined information indicating a position of the detector relative to the reference element coupled to the imaging device and the virtual position of the reference element coupled to the imaging device.

At block 1920, processing circuitry 3320 determines a first virtual position of a tracked instrument while the tracked instrument is at a first physical position between the emitter and the detector. In some embodiments, the system includes a tracking camera. Determining the first virtual position of the tracked instrument includes: determining information about a shape of the tracked instrument relative to a reference element coupled to the tracked instrument; capturing, via the camera, an image of the reference element coupled to the tracked instrument; determining a virtual position of the reference element coupled to the tracked instrument (e.g., relative to the DRB) based on the image of the reference element coupled to the tracked instrument; and determining the first virtual position of the tracked instrument based on the shape of the tracked instrument and the reference element coupled to the tracked instrument.

In additional or alternative embodiments, determining the information about the shape of the tracked instrument includes determining an intended position of a tip of the tracked instrument relative to the reference element coupled to the tracked instrument.

At block 1925, processing circuitry 3320 determines a first expected image of the tracked instrument. In some embodiments, the first expected image of the tracked instrument is determined by simulating operation of the emitter and the detector based on the first virtual position of the emitter, the first virtual position of the detector, the first virtual position of the tracked instrument, and a predetermined shape of the tracked instrument.

At block 1930, processing circuitry 3320 obtains a first image of the tracked instrument. In some embodiments, obtaining the first image of the tracked instrument includes receiving the first image from the imaging device.

At block 1935, processing circuitry 3320 rotates the imaging device (including the emitter and the detector). In some examples, the imaging device includes a C-arm or an O-arm imaging device.

At block 1940, processing circuitry 3320 determines a second virtual position of the emitter. In some embodiments, determining the second virtual position of the emitter includes receiving the second virtual position from a tracking system.

At block 1945, processing circuitry 3320 determines a second virtual position of the detector. In some embodiments, determining the second virtual position of the detector includes receiving the second virtual position from a tracking system.

At block 1950, processing circuitry 3320 determines a second virtual position of the tracked instrument while the tracked instrument is at a second physical position between the emitter and the detector. In some embodiments, determining the second virtual position of the tracked instrument includes receiving the second virtual position from a tracking system.

In additional or alternative embodiments, the first virtual position of the tracked instrument is the second virtual position of the tracked instrument. For example, the imaging device can include at least one of a C-arm and a O-arm and responsive to obtaining the first image, the imaging device can be rotated (block 1935) such that the second virtual position of the emitter is different than the first virtual position of the emitter and that the second virtual position of the detector is different than the first virtual position of the detector. As a result an image of the tracked instrument from a different perspective can be taken without moving the tracked instrument.

In additional or alternative embodiments, the first virtual position of the tracked instrument is different than the second virtual position of the tracked instrument. The first virtual position of the emitter is the second virtual position of the emitter The first virtual position of the detector is the second virtual position. For example, without rotating the imaging device an image of the tracked instrument can be taken from a different perspective by moving the tracked instrument.

At block 1955, processing circuitry 3320 determines a second expected image of the tracked instrument. In some embodiments, the second expected image of the tracked instrument is determined by simulating operation of the emitter and the detector based on the second virtual position of the emitter, the second virtual position of the detector, the second virtual position of the tracked instrument, and a predetermined shape of the tracked instrument.

At block 1960, processing circuitry 3320 obtains a second image of the tracked instrument. In some embodiments, obtaining the second image of the tracked instrument includes receiving the second image from the imaging device.

At block 1965, processing circuitry 3320 determines whether the tracked instrument is accurate based on the first expected image, the second expected image, the first image, and the second image. In some embodiments, the first expected image, the second expected image, the first image, and the second image each include an image of the tip of the tracked instrument.

At block 1970, processing circuitry 3320 performs an action based on whether the tracked instrument is accurate. In some embodiments, determining whether the tracked instrument is accurate includes determining that a difference between the first expected image and/or the second expected image and the first image and/or the second image exceeds a predetermined threshold. In some examples, performing the action includes outputting an indication that the tracked instrument is not suitable for use. In additional or alternative examples, performing the action includes calibrating a tracking system used to track the tracked instrument using at least one of the first expected image, the second expected image, the first image, and the second image.

Various operations of FIG. 19 may be optional. For example, blocks 1935, 1940, 1945, and 1970 may be optional in some embodiments.

Embodiments that include performing an accuracy check and/or calibrating a tracked instrument based on comparison of an actual position with an expected position on a display device are described below.

In some embodiments, a display screen is available to show tracked instruments. In some examples, the display screen is near the surgical area and is already covered with sterile drape. The screen may be large size (e.g., 22 inches or larger). A reference element can be coupled to the display screen to allow it to be tracked by a navigation camera. A large reference element array can yield improved accuracy of tracking and, in some examples, due to the large physical size, more than four optical markers can be used to improve the fidelity of tracking.

In additional or alternative embodiments, when a user brings a navigated instrument near the display screen, its position with respect to the reference element on the display screen is calculated. The theoretical position of the tracked tip of the instrument CAD is then shown on the display screen. The user can visually compare the accuracy of the physical position of the instrument tip with the position displayed on the screen. With aid of a virtual measurement tool, the user can then assess the accuracy.

Figure 17:
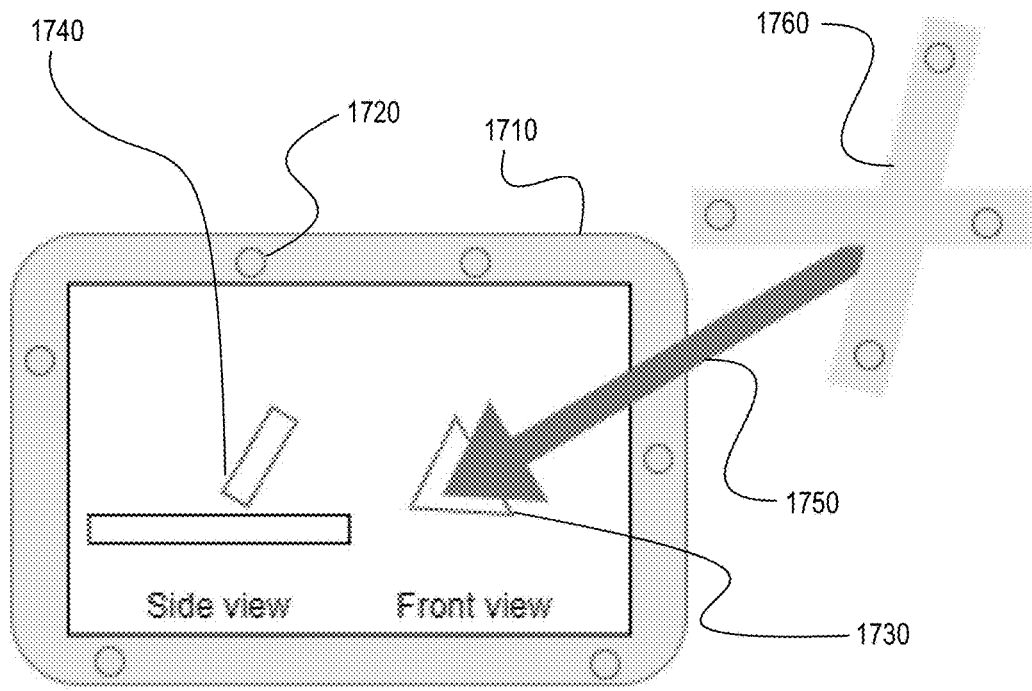
FIG. 17 is a schematic diagram of a display device configured to show an expected position of a tracked instrument according to some embodiments.

FIG. 17 illustrates an example of a display device 1710 displaying a theoretical position (front view 1730 and side view 1740) of the tip of a tracked instrument 1750. The display device 1710 has reference elements 1720 and the tracked instrument 1750 has reference elements 1760 for being tracked by a navigation camera.

In this example, the front view 1730 of the theoretical position of the tip of the tracked instrument 1750 is shown as a hollow triangle on the right half of the screen. The left half of the screen shows a side view 1740 of the theoretical position of the tip of the tracked instrument 1750, allowing assessment of theoretical height above the screen of the tracked instrument 1750.

In some embodiments, the display device can be used for performing an accuracy check of any shape of tracked instrument tip. Even unconventional tips, such as a hook can be easily visualized on the screen.

In additional or alternative embodiments, the same display screen can be used for an accuracy check of multiple instruments. In additional or alternative embodiments, the screen array is unlikely to be damaged during surgery due to splatter of blood or other smudges, since it is typically much farther from the surgical field compared to tracked instruments.

In additional or alternative embodiments, if the surface of the display screen can sense the touch of the instrument tip, the accuracy can be calculated as well instead of relying on visual assessment.

In some embodiments, using the display device to perform an accuracy check of a tracked instrument can improve fidelity of reference element array used for accuracy check and consistency of accuracy checks.

In additional or alternative embodiments, using the display device to perform an accuracy check of a tracked instrument can improve accuracy check workflow for instruments without a sharp, straight tip.

In additional or alternative embodiments, using the display device to perform an accuracy check of a tracked instrument can allow user for visual inspection and assessment of accuracy.

Figure 20:
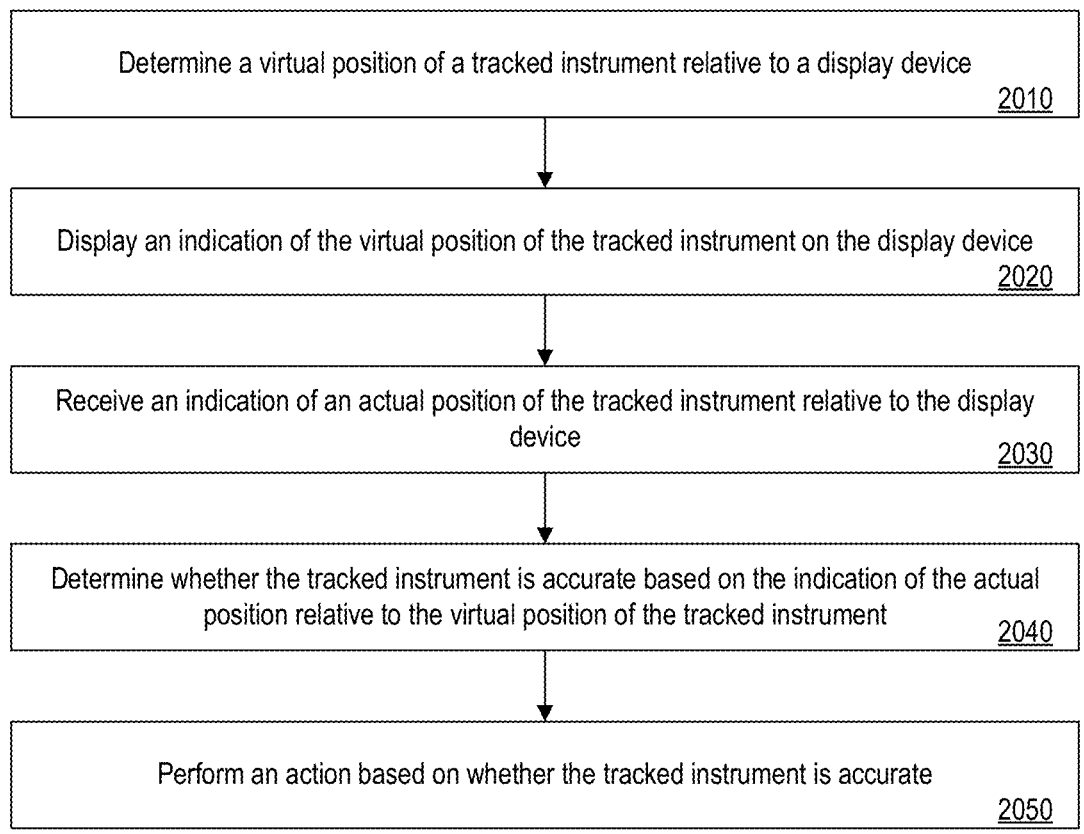

FIG. 20 illustrates an example of operations performed by a system to perform an accuracy check and/or calibration of a tracked instrument based on displaying a virtual position of the tracked instrument on a display device. Although the operations are described below as being performed by the accuracy and calibration module 3300, any suitable system (e.g., an imaging system or a tracking system) can perform these operations.

At block 2010, processing circuitry 3320 determines a virtual position of a tracked instrument relative to a display device.

At block 2020, processing circuitry 3320 displays an indication of the virtual position of the tracked instrument on the display device. In some embodiments, the processing circuitry determines an intended shape of the tracked instrument. For example, an accurate and/or undamaged shape of the tracked instrument. Displaying the indication of the virtual position of the tracked instrument includes: displaying on a first part of the display device, a first portion of the intended shape of the tracked instrument in a front view perspective based on the virtual position of the tracked instrument; and displaying on a second part of the display device, a second portion of the tracked instrument in a side view perspective based on the virtual position of the tracked instrument.

At block 2030, processing circuitry 3320 receives an indication of an actual position of the tracked instrument relative to the display device. In some embodiments, receiving the actual position of the tracked instrument includes receiving an indication from a user.

At block 2040, processing circuitry 3320 determines whether the tracked instrument is accurate based on the indication of the actual position relative to the virtual position of the tracked instrument.

At block 2050, processing circuitry 3320 performs an action based on whether the tracked instrument is accurate. In some embodiments, performing the action includes, responsive to determining whether the tracked instrument is accurate, outputting an indication of whether the tracked instrument is suitable for use. In additional or alternative embodiments, performing the action includes, responsive to determining whether the tracked instrument is accurate, calibrating a tracking system used to track the tracked instrument using at least one of the virtual position of the tracked instrument and the actual position of the tracked instrument.

Various operations of FIG. 20 may be optional. For example, block 2050 may be optional in some embodiments.

Further Definitions and Embodiments

In the above-description of various embodiments of present inventive concepts, it is to be understood that the terminology used herein is for the purpose of describing particular embodiments only and is not intended to be limiting of present inventive concepts. Unless otherwise defined, all terms (including technical and scientific terms) used herein have the same meaning as commonly understood by one of ordinary skill in the art to which present inventive concepts belongs. It will be further understood that terms, such as those defined in commonly used dictionaries, should be interpreted as having a meaning that is consistent with their meaning in the context of this specification and the relevant art and will not be interpreted in an idealized or overly formal sense expressly so defined herein.

When an element is referred to as being "connected", "coupled", "responsive", or variants thereof to another element, it can be directly connected, coupled, or responsive to the other element or intervening elements may be present. In contrast, when an element is referred to as being "directly connected", "directly coupled", "directly responsive", or variants thereof to another element, there are no intervening elements present. Like numbers refer to like elements throughout. Furthermore, "coupled", "connected", "responsive", or variants thereof as used herein may include wirelessly coupled, connected, or responsive. As used herein, the singular forms "a", "an" and "the" are intended to include the plural forms as well, unless the context clearly indicates otherwise. Well-known functions or constructions may not be described in detail for brevity and/or clarity. The term "and/or" includes any and all combinations of one or more of the associated listed items.

It will be understood that although the terms first, second, third, etc. may be used herein to describe various elements/operations, these elements/operations should not be limited by these terms. These terms are only used to distinguish one element/operation from another element/operation. Thus, a first element/operation in some embodiments could be termed a second element/operation in other embodiments without departing from the teachings of present inventive concepts. The same reference numerals or the same reference designators denote the same or similar elements throughout the specification.

As used herein, the terms "comprise", "comprising", "comprises", "include", "including", "includes", "have", "has", "having", or variants thereof are open-ended, and include one or more stated features, integers, elements, steps, components or functions but does not preclude the presence or addition of one or more other features, integers, elements, steps, components, functions or groups thereof. Furthermore, as used herein, the common abbreviation "e.g.", which derives from the Latin phrase "exempli gratia," may be used to introduce or specify a general example or examples of a previously mentioned item, and is not intended to be limiting of such item. The common abbreviation "i.e.", which derives from the Latin phrase "id est," may be used to specify a particular item from a more general recitation.

Example embodiments are described herein with reference to block diagrams and/or flowchart illustrations of computer-implemented methods, apparatus (systems and/or devices) and/or computer program products. It is understood that a block of the block diagrams and/or flowchart illustrations, and combinations of blocks in the block diagrams and/or flowchart illustrations, can be implemented by computer program instructions that are performed by one or more computer circuits. These computer program instructions may be provided to a processor circuit of a general purpose computer circuit, special purpose computer circuit, and/or other programmable data processing circuit to produce a machine, such that the instructions, which execute via the processor of the computer and/or other programmable data processing apparatus, transform and control transistors, values stored in memory locations, and other hardware components within such circuitry to implement the functions/acts specified in the block diagrams and/or flowchart block or blocks, and thereby create means (functionality) and/or structure for implementing the functions/acts specified in the block diagrams and/or flowchart block(s).

These computer program instructions may also be stored in a tangible computer-readable medium that can direct a computer or other programmable data processing apparatus to function in a particular manner, such that the instructions stored in the computer-readable medium produce an article of manufacture including instructions which implement the functions/acts specified in the block diagrams and/or flowchart block or blocks. Accordingly, embodiments of present inventive concepts may be embodied in hardware and/or in software (including firmware, resident software, microcode, etc.) that runs on a processor such as a digital signal processor, which may collectively be referred to as "circuitry," "a module" or variants thereof.

It should also be noted that in some alternate implementations, the functions/acts noted in the blocks may occur out of the order noted in the flowcharts. For example, two blocks shown in succession may in fact be executed substantially concurrently or the blocks may sometimes be executed in the reverse order, depending upon the functionality/acts involved. Moreover, the functionality of a given block of the flowcharts and/or block diagrams may be separated into multiple blocks and/or the functionality of two or more blocks of the flowcharts and/or block diagrams may be at least partially integrated. Finally, other blocks may be added/inserted between the blocks that are illustrated, and/or blocks/operations may be omitted without departing from the scope of inventive concepts. Moreover, although some of the diagrams include arrows on communication paths to show a primary direction of communication, it is to be understood that communication may occur in the opposite direction to the depicted arrows.

Many variations and modifications can be made to the embodiments without substantially departing from the principles of the present inventive concepts. All such variations and modifications are intended to be included herein within the scope of present inventive concepts. Accordingly, the above disclosed subject matter is to be considered illustrative, and not restrictive, and the appended examples of embodiments are intended to cover all such modifications, enhancements, and other embodiments, which fall within the spirit and scope of present inventive concepts. Thus, to the maximum extent allowed by law, the scope of present inventive concepts are to be determined by the broadest permissible interpretation of the present disclosure including the following examples of embodiments and their equivalents, and shall not be restricted or limited by the foregoing detailed description.

What is claimed is:

1. A system configured to perform an accuracy check of a tracked surgical instrument, the system comprising:
a camera;
processing circuitry;
wherein the camera is coupled to the processing circuitry; and
memory coupled to the processing circuitry and having instructions stored therein that are executable by the processing circuitry to cause the system to perform operations including:
determining information about a shape of a touch sensor relative to a reference element coupled to the touch sensor;
capturing, via the camera, an image of the reference element coupled to the touch sensor;

determining a virtual position of the reference element coupled to the touch sensor based on the image of the reference element coupled to the touch sensor, the virtual position of the reference element coupled to the touch sensor including a virtual location and a virtual pose of the reference element coupled to the touch sensor;

determining a virtual position within a virtual space of the touch sensor based on the information about the shape of the touch sensor and the virtual position of the reference element coupled to the touch sensor, the virtual position of the touch sensor including a virtual location and a virtual pose of the touch sensor;

determining information about a shape of the tracked surgical instrument relative to a reference element coupled to the tracked surgical instrument;

capturing, via the camera, an image of the reference element coupled to the tracked surgical instrument;

determining a virtual position of the reference element coupled to the tracked surgical instrument based on the image of the reference element coupled to the tracked surgical instrument, the virtual position of the reference element coupled to the tracked surgical instrument including a virtual location and a virtual pose of the reference element coupled to the tracked surgical instrument;

determining a virtual position within the virtual space of the tracked surgical instrument based on the shape of the tracked surgical instrument and the reference element coupled to the tracked surgical instrument, the virtual position of the tracked surgical instrument including a virtual location and a virtual pose of the tracked surgical instrument;

determining a point of contact on the touch sensor between the tracked surgical instrument and the touch sensor;

determining an expected point of contact on the touch sensor between the tracked surgical instrument and the touch sensor based on the virtual position of the touch sensor and the virtual position of the tracked surgical instrument; and determining whether the tracked surgical instrument is accurate based on a difference between the point of contact and the expected point of contact.

2. The system of claim 1, wherein determining the information about the shape of the tracked surgical instrument includes determining an intended position of a tip of the tracked surgical instrument relative to the reference element coupled to the tracked surgical instrument, wherein determining the point of contact on the touch sensor includes determining a point of contact between the tip of the tracked surgical instrument and the touch sensor, and wherein determining the expected point of contact on the touch sensor includes determining a point of contact between the tip of the tracked surgical instrument and the touch sensor based on the virtual position of the touch sensor and the virtual position of the tracked surgical instrument.

3. The system of claim 1, wherein the system comprises:

the touch sensor coupled to the processing circuitry, the touch sensor including a touchscreen, wherein determining the point of contact includes detecting a location on the touchscreen that the tracked surgical instrument is touching.

4. The system of claim 3, wherein the touch sensor includes a plurality of touch sensors coupled together to form an opening, and wherein determining the point of contact on the touch sensor includes determining a plurality of points of contact, each point of contact between one of the touch sensors of the plurality of touch sensors and the tracked surgical instrument while the tracked surgical instrument is positioned in the opening.

5. The system of claim 1, wherein determining the point of contact on the touch sensor includes determining a plurality of points of contact between the tracked surgical instrument and the touch sensor, wherein determining the expected point of contact on the touch sensor includes determining a plurality of expected points of contact between the tracked surgical instrument and the touch sensor based on the virtual position of the touch sensor and the virtual position of the tracked surgical instrument, and wherein determining whether the tracked surgical instrument is accurate includes determining whether the tracked surgical instrument is accurate based on a difference between the plurality of points of contact and the plurality of expected points of contact.

6. The system of claim 1, wherein determining whether the tracked surgical instrument is accurate includes determining that the difference exceeds a predetermined threshold, the operations further including:
outputting an indication that the tracked surgical instrument is not suitable for use.

7. The system of claim 1, wherein determining whether the tracked surgical instrument is accurate includes determining that the difference exceeds a predetermined threshold, the operations further including:
calibrating a tracking system used to track the tracked surgical instrument using at least one of the point of contact, the expected point of contact, and the difference.

8. The system of claim 1, wherein the system comprises:

a display device coupled to the processing circuitry, the display device including the touch sensor, the operations further including:
displaying, via the display device, an indication of the expected point of contact, wherein determining the point of contact on the display device between the tracked surgical instrument and the display device includes receiving an indication of the point of contact on the display device from a user.

* * * * *